(12) United States Patent
Moroz et al.

(10) Patent No.: US 10,000,737 B2
(45) Date of Patent: Jun. 19, 2018

(54) GENERATION OF CYTOTOXIC TUMOR SPECIFIC CELL LINES AND USES THEREOF

(71) Applicant: Ramot at Tel-Aviv University Ltd., Tel-Aviv (IL)

(72) Inventors: Chaya Moroz, Tel-Aviv (IL); Inna Solodeev, Ramat-Gan (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 248 days.

(21) Appl. No.: 14/765,570

(22) PCT Filed: Feb. 3, 2014

(86) PCT No.: PCT/IL2014/050114
§ 371 (c)(1),
(2) Date: Aug. 4, 2015

(87) PCT Pub. No.: WO2014/118785
PCT Pub. Date: Aug. 7, 2014

(65) Prior Publication Data
US 2016/0122715 A1 May 5, 2016

Related U.S. Application Data

(60) Provisional application No. 61/760,215, filed on Feb. 4, 2013.

(51) Int. Cl.
| | | |
|---|---|---|
| *A61K 38/00* | (2006.01) | |
| *C12N 5/00* | (2006.01) | |
| *C07K 14/00* | (2006.01) | |
| *C12N 5/0783* | (2010.01) | |
| *A61K 35/17* | (2015.01) | |

(52) U.S. Cl.
CPC ............ *C12N 5/0638* (2013.01); *A61K 35/17* (2013.01); *C12N 2501/2302* (2013.01); *C12N 2501/998* (2013.01); *C12N 2502/30* (2013.01)

(58) Field of Classification Search
None
See application file for complete search history.

(56) References Cited

U.S. PATENT DOCUMENTS

| 4,882,270 | A | 11/1989 | Moroz |
| 5,283,177 | A | 2/1994 | Moroz et al. |
| 7,217,686 | B1 | 5/2007 | Moroz |
| 2013/0252905 | A1 | 9/2013 | Moroz |
| 2016/0213765 | A1 | 6/2016 | Moroz |

FOREIGN PATENT DOCUMENTS

| WO | WO 2007/131218 | 11/2007 |
| WO | WO 2013/140389 | 9/2013 |
| WO | WO 2014/118785 | 8/2014 |

OTHER PUBLICATIONS

Mikayama et al. PNAS, 1993. 90: 10056-10060.*
Burgess et al ., J Cell Biol. 111:2129-2138, 1990.*
Whisstock et al ( Quarterly Review of Biophysics, 2003, 36, pp. 307-340.*
Wang et al. JBC, 2001 276:49213-49220.*
Bowie et al. Science, 247:1306-1310, 1990, p. 1306, col. 2).*
Supplementary European Search Report and the European Search Opinion dated Jul. 12, 2016 From the European Patent Office Re. Application No. 1475808.7.
Komoriya et al. "Biologically Active Synthetic Fragments of Epidermal Growth Factor: Localization of a Major Receptor-Binding Region", Proc. Natl. Acad. Sci. USA, XP055284714, 81(5): 1351-1355, Mar. 1, 1984.
Solodeev et al. "The Novel C24D Synthetic Polypeptide Inhibits Binding of Placenta Immunosuppressive Ferritin to Human T Cells and Elicits Anti-Breast Cancer Immunity In Vitro and In Vivo", Neoplasia, XP055284392, 16(9): 741-750, Sep. 1, 2014.
Advisory Action Before the Filing of an Appeal Brief dated Nov. 16, 2015 From the US Patent and Trademark Office Re. U.S. Appl. No. 13/792,102.
International Preliminary Report on Patentability dated Oct. 2, 2014 From the International Bureau of WIPO Re. Application No. PCT/IL2013/050218.
International Preliminary Report on Patentability dated Aug. 13, 2015 From the International Bureau of WIPO Re. Application No. PCT/IL2014/050114.
International Search Report and the Written Opinion dated Jun. 24, 2013 From the International Searching Authority Re. Application No. PCT/IL2013/050218.
International Search Report and the Written Opinion dated May 27, 2014 From the International Searching Authority Re. Application No. PCT/IL2014/050114.
Official Action dated Aug. 14, 2015 From the US Patent and Trademark Office Re. U.S. Appl. No. 13/792,102.
Official Action dated Feb. 26, 2015 From the US Patent and Trademark Office Re. U.S. Appl. No. 13/792,102.
Supplementary European Search Report and the European Search Opinion dated Dec. 1, 2015 From the European Patent Office Re. Application No. 13764023.1.
Halpern et al. "Antibodies to Placental Immunoregulatory Ferritin With Transfer of Polyclonal Lymphocytes Arrest MCF-7 Human Beast Cancer Growth in a Nude Mouse Mode", Neoplasia, 9(6): 487-494, Jun. 2007. Abstract, P.487, Last Para, p. 492-493, Figs.7,8.
Moroz et al. "PLIF, A Novel Human Ferritin Subunit From Placenta With Immunosuppressive Activity", The Journal of Biological Chemistry, 277(15): 12901-12905, Apr. 12, 2002.

(Continued)

*Primary Examiner* — Michail Belyavskyi

(57) ABSTRACT

An in-vitro method of activating T cells is disclosed. The method comprises incubating T cells with pathogenic cells in the presence of a multimeric peptide comprising at least two peptide monomers linked to one another, each of the at least two peptide monomers comprising at least 6 consecutive amino acids from the amino acid sequence as set forth in SEQ ID NO: 1, wherein the at least two peptide monomers are each no longer than 30 amino acids, wherein the multimeric peptide is capable of reducing binding of PLIF to human leukocytes under conditions which allow expansion of the T cells.

9 Claims, 14 Drawing Sheets
(11 of 14 Drawing Sheet(s) Filed in Color)

(56) References Cited

OTHER PUBLICATIONS

Nahum et al. "Blocking of the Placental Immune-Modulatory Ferritin Activates Th1 Type Cytokines and Affects Placenta Development, Fetal Growth and the Pregnancy Outcome", Human Reproduction, 19(3): 715-722, 2004. Abstract, p. 717-720, Fig.6.

* cited by examiner

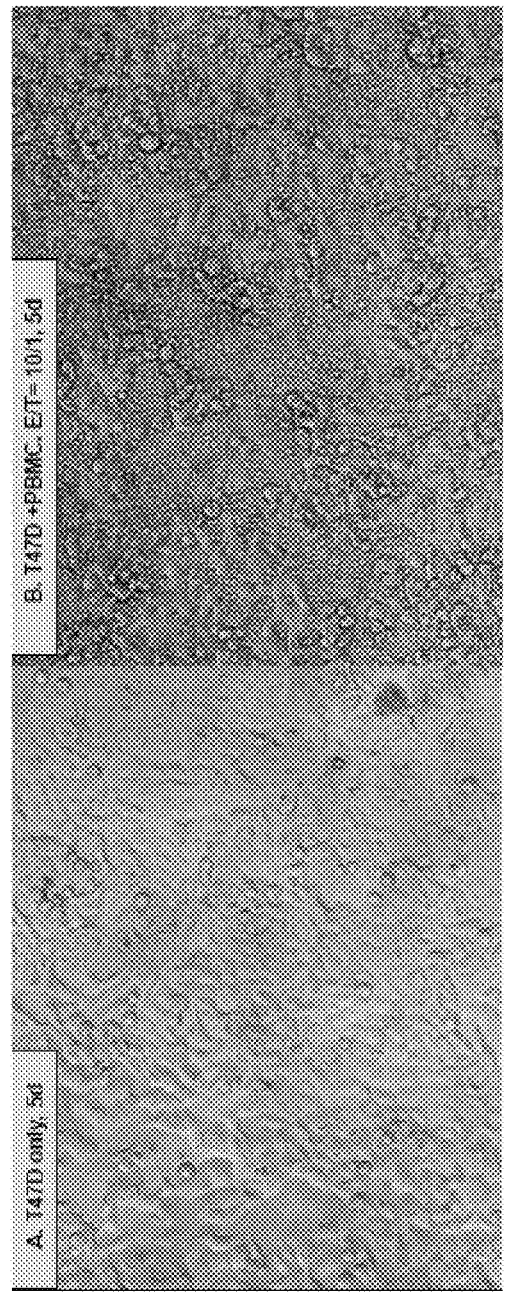
FIG. 2A
FIG. 2B
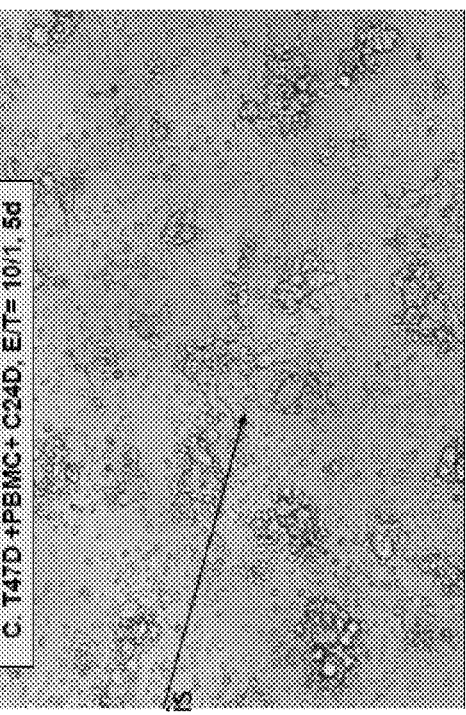
FIG. 2C

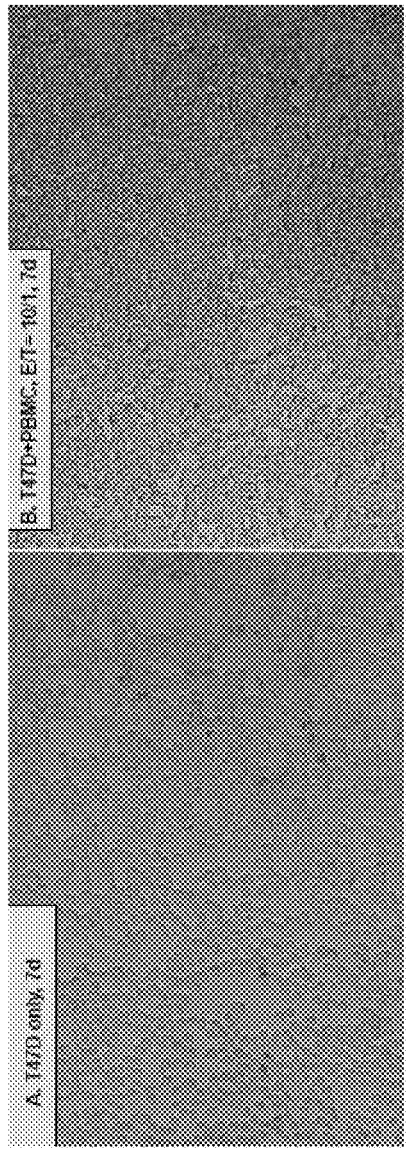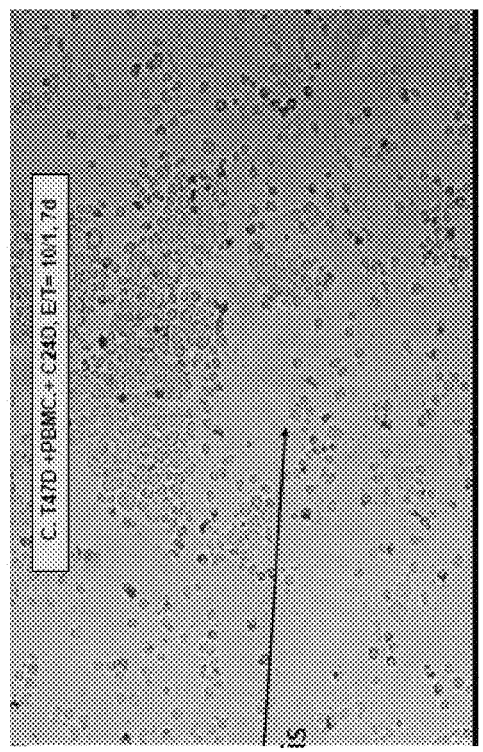
FIG. 3A
FIG. 3B
FIG. 3C
Tumor cytolysis

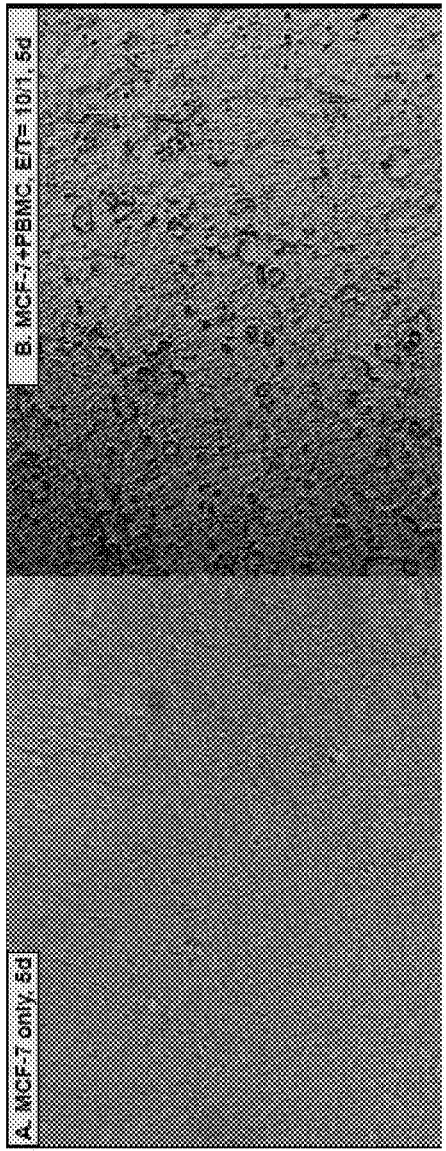
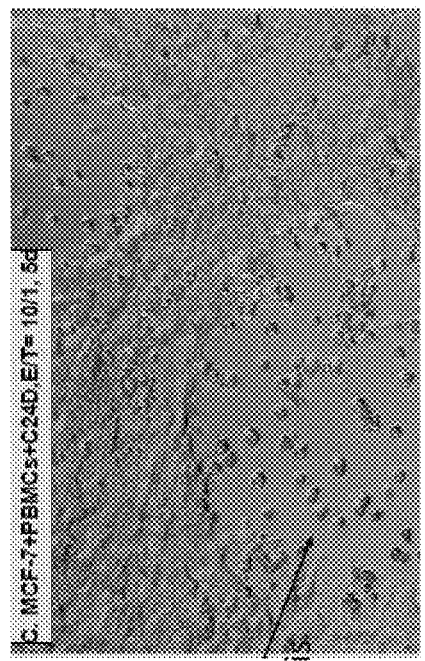
FIG. 4A
FIG. 4B
FIG. 4C

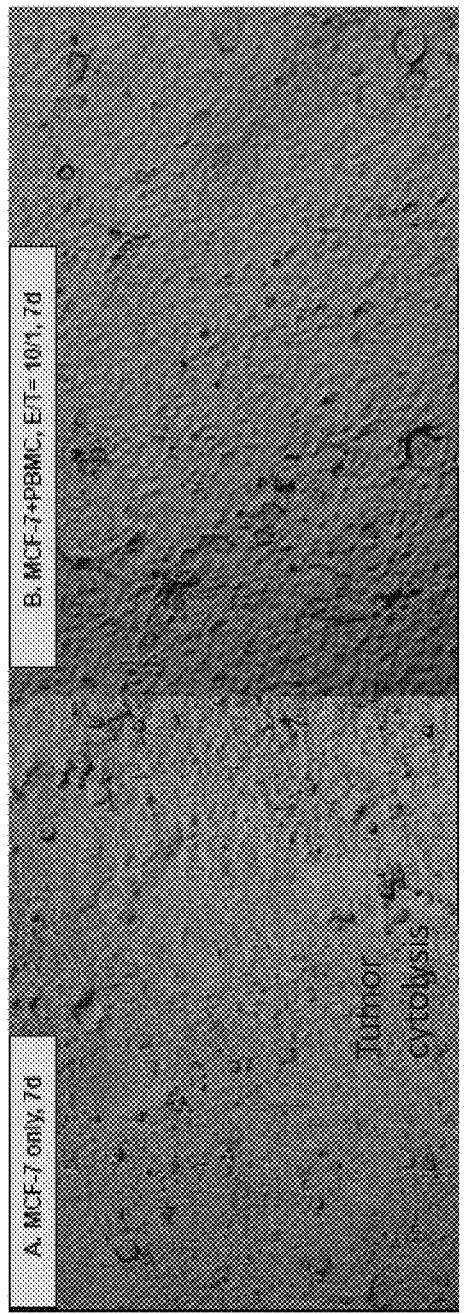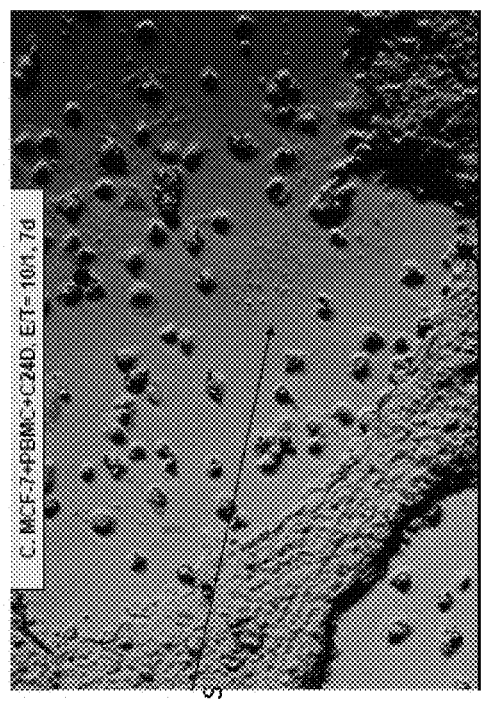
FIG. 5A
FIG. 5B
FIG. 5C

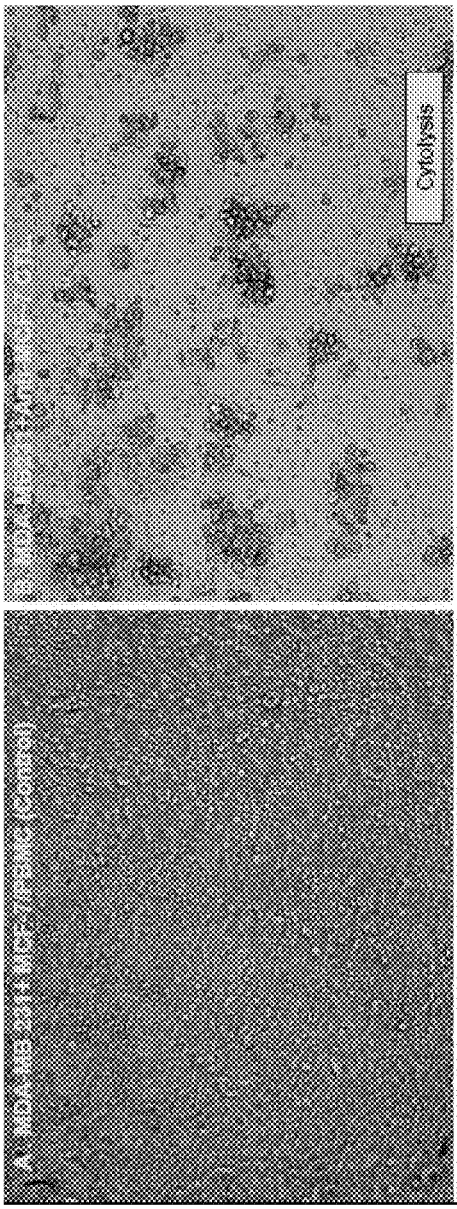
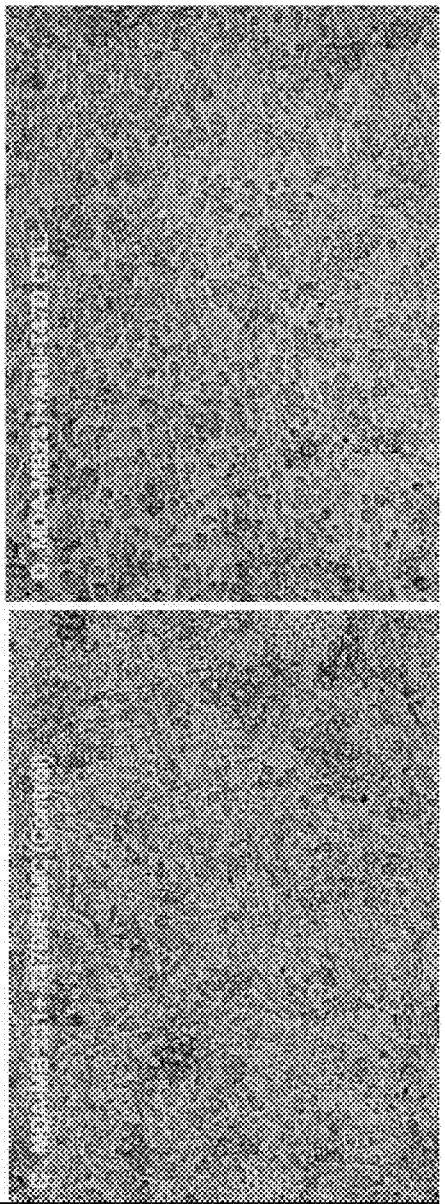
FIG. 11A  FIG. 11B  FIG. 11C  FIG. 11D

GENERATION OF CYTOTOXIC TUMOR SPECIFIC CELL LINES AND USES THEREOF

RELATED APPLICATIONS

This application is a National Phase of PCT Patent Application No. PCT/IL2014/050114 having International filing date of Feb. 3, 2014, which claims the benefit of priority under 35 USC § 119(e) of U.S. Provisional Patent Application No. 61/760,215 filed on Feb. 4, 2013. The contents of the above applications are all incorporated by reference as if fully set forth herein in their entirety.

SEQUENCE LISTING STATEMENT

The ASCII file, entitled 63418SequenceListing.txt, created on Jul. 22, 2015, comprising 22,302 bytes, submitted concurrently with the filing of this application is incorporated herein by reference.

FIELD AND BACKGROUND OF THE INVENTION

The present invention, in some embodiments thereof, relates to generation of cytotoxic tumor specific cell lines using Placental Immunoregulatory Ferritin (PLIF) peptides.

Clinical studies on tumor cell-based vaccines are based on the concept that autologous or allogeneic tumor cells express many tumor-associated antigens (TAA). The MHC class I system, along with the endogenous peptides presented on the cell surface are unique markers used by effector CD8+ T cells to discriminate normal cells from diseased cells. MHC class I complexes are constitutively expressed by all nucleated cells in the body. The MHC system includes Ag-processing machinery that processes and presents peptides in the context of MHC molecules on to the cell surface. Thus, cytotoxic T cells made against TAA complexes (TAA/MHC) that mediate anti tumor effects could serve as a novel modality for cancer treatment.

In order to develop immunotherapy for cancer, it is of the utmost importance to have representative target cell lines that present relevant levels of peptides from TAAs on HLA class I molecules. Since HLA-A*0201 is the most common HLA class I molecule in humans, most studies describing the generation of T cells against cancer cell TAAs have focused on HLA-A*0201-restricted peptides.

Several human studies in recent years have demonstrated that the infusion of tumor-specific cytotoxic T cell lines and clones may have a positive clinical effect on diverse malignant diseases, such as colorectal cancer, Hodgkin's lymphoma and nasopharyngeal carcinoma. In most studies documented, the amount of cytotoxic T cell lines required for therapy range from $1\times10^7$ to $1\times10^8$ per infusion, and most treatment regimens require several cycles of adoptive transfer.

Tumor-specific cytotoxic lymphocytes are usually expanded from peripheral blood mononuclear cells (PBMC) taken from tumor-bearing patients. These are expanded using antigen-presenting cells pulsed with irradiated tumor cells, tumor peptides, tumor lysates or fused tumor cells, resulting in the expansion of MHC class I-restricted cytotoxic T cell lines over several weeks of culture. Tumor-specific cytotoxic T cell lines can also be derived as a subpopulation of tumor-infiltrating lymphocytes by modifying the methodologies, including a purification step based on the selection of CD8 T cells.

In human clinical trials, infusion of tumor-specific T cells derived from tumor-infiltrating lymphocytes or draining lymph nodes has shown limited but encouraging clinical responses in specific settings. Unfortunately, the ability to expand tumor antigen-specific T cells ex vivo from cancer patients is technically difficult due to numerous obstacles, including initiating cultures with low numbers of tumor-specific T cells and the physical inability to obtain tumor-infiltrating lymphocytes from patients with the most common malignancies.

Placenta Immunomodulatory Factor (PLIF) is a protein composed of 165 amino acids. Of these, 117 match the ferritin heavy chain sequence, whereas the C-terminal 48 amino acids (C48) has a sequence which is not related to ferritin. It has been shown that the subcloned recombinant C48 peptide exhibits the bioactivity and therapeutic properties of PLIF [Moroz et al, J. Biol. Chem. 2002, 277, 12901-12905].

PLIF is expressed in the feto-maternal interface in both decidual mononuclear cells and syncytiotrophoblast cells. C48/PLIF binds to macrophages and activated T cells, inducing high levels of IL-10, and acts as a regulatory cytokine. It governs the balance between Th1/Th2 cytokines, which is essential for induction of tolerance during pregnancy. A significantly high correlation was observed between low levels of serum PLIF and the different pathological pregnancy conditions: early pregnancy failures; pregnancies complicated with abortion; intrauterine growth restriction (IUGR); and women at risk for developing pre-eclampsia.

It has been shown that PLIF is upregulated and expressed in malignant cells such as Hodgkin's and non-Hodgkin's lymphoma, acute lymphatic leukemia (ALL), human breast cancer tissues, and breast cancer cell lines (T47D and MCF-7), but not in benign breast disease. Similar to the embryo, PLIF manipulates the cytokine network and immune response, enabling immune escape.

Experiments have been performed to restore T cell immunity and induce rejection of breast cancer by neutralizing C48/PLIF. Rabbit anti-C48 polyclonal antibodies injected intraperitoneally (i.p.) into immune compromised Nude mice engrafted with MCF-7 human breast cancer cells resulted in growth arrest associated with human cell apoptosis and massive intra-tumor lymphocytic infiltration. This was accompanied by activation of INF-γ, thus affecting the cytokine network and leading to breakdown of tolerance.

Synthetic PLIF dimeric peptides are disclosed in U.S. Patent Application No. 61/614,110 for the treatment of cancer.

Additional background art includes U.S. Pat. No. 4,882,270 which discloses a method for detecting breast cancer, by using antibodies against isoferritin placental protein.

SUMMARY OF THE INVENTION

According to an aspect of some embodiments of the present invention there is provided an in-vitro method of activating T cells, the method comprising incubating T cells with pathogenic cells in the presence of a multimeric peptide comprising at least two peptide monomers linked to one another, each of the at least two peptide monomers comprising at least 6 consecutive amino acids from the amino acid sequence as set forth in SEQ ID NO: 1, wherein the at least two peptide monomers are each no longer than 30 amino acids, wherein the multimeric peptide is capable of reducing binding of PLIF to human leukocytes under conditions which allow expansion of the T cells.

According to an aspect of some embodiments of the present invention there is provided an in vitro method of increasing the cytotoxicity of T cells comprising incubating pathogenic cells which have an upregulated amount of Placenta Immunomodulatory Factor (PLIF) as compared to healthy cells with T cells in the presence of a multimeric peptide comprising at least two peptide monomers linked to one another, each of the at least two peptide monomers comprising at least 6 consecutive amino acids from the amino acid sequence as set forth in SEQ ID NO: 1, wherein the at least two peptide monomers are each no longer than 30 amino acids, wherein the multimeric peptide is capable of reducing binding of PLIF to human leukocytes under conditions which allow for the generation of activated T cells that are cytotoxic to the pathogenic cells, thereby increasing the cytotoxicity of the T cells.

According to an aspect of some embodiments of the present invention there is provided an in vitro method of generating a cytotoxic T cell line comprising:

(a) incubating pathogenic cells which have an upregulated amount of Placenta Immunomodulatory Factor (PLIF) as compared to healthy cells with T cells in the presence of a multimeric peptide comprising at least two peptide monomers linked to one another, each of the at least two peptide monomers comprising at least 6 consecutive amino acids from the amino acid sequence as set forth in SEQ ID NO: 1, wherein the at least two peptide monomers are each no longer than 30 amino acids, wherein the multimeric peptide is capable of reducing binding of PLIF to human leukocytes under conditions which allow for the generation of activated T cells that are cytotoxic to the pathogenic cells; and (b) expanding the activated T cells, thereby generating the cytotoxic T cell line.

According to an aspect of some embodiments of the present invention there is provided an isolated cytotoxic T cell line which comprises a multimeric peptide attached to an outer surface of T cells of the T cell line, the multimeric peptide comprising at least two peptide monomers linked to one another, each of the at least two peptide monomers comprising at least 6 consecutive amino acids from the amino acid sequence as set forth in SEQ ID NO: 1, wherein the at least two peptide monomers are each no longer than 30 amino acids, wherein the multimeric peptide is capable of reducing binding of PLIF to human leukocytes.

According to an aspect of some embodiments of the present invention there is provided an isolated cytotoxic T cell line generated according to the methods described herein.

According to an aspect of some embodiments of the present invention there is provided a pharmaceutical composition comprising the cytotoxic T cell lines described herein.

According to an aspect of some embodiments of the present invention there is provided a method of treating a disease which is amenable to treatment by adoptive immunotherapy in a subject in need thereof, the method comprising administering to the subject a therapeutically effective amount of the cytotoxic T cell line described herein, thereby treating the disease.

According to an aspect of some embodiments of the present invention there is provided a cytotoxic T cell line generated according to the method described herein for treating a disease caused by a pathogenic cell population amenable to cytotoxic T cell therapy.

According to an aspect of some embodiments of the present invention there is provided a bank comprising a plurality of the cytotoxic T cell lines.

According to some embodiments of the invention, the method further comprises expanding the activated T cells.

According to some embodiments of the invention, the expanding is effected using interleukin 2 (IL-2).

According to some embodiments of the invention, the pathogenic cells comprise cancer cells.

According to some embodiments of the invention, the cancer cells comprise breast cancer cells.

According to some embodiments of the invention, the breast cancer cells comprise cells of the T47D or MCF-7 cell lines.

According to some embodiments of the invention, the T cells are comprised in peripheral mononuclear blood cells (PBMCs).

According to some embodiments of the invention, the peptide is capable of increasing INF-γ secretion from activated leukocytes.

According to some embodiments of the invention, the peptide is a dimer.

According to some embodiments of the invention, each of the at least two peptide monomers comprise no more than 15 consecutive amino acids from the amino acid sequence as set forth in SEQ ID NO: 1.

According to some embodiments of the invention, the at least two peptides comprise an identical amino acid sequence.

According to some embodiments of the invention, each of the at least two peptide monomers is attached to a Cysteine (Cys) residue.

According to some embodiments of the invention, the caboxy end of the at least two peptide monomers is attached to the Cys residue.

According to some embodiments of the invention, each of the two peptide monomers are attached via a non-peptide linker.

According to some embodiments of the invention, the at least two peptide monomers are linked to one another by a disulfide bond.

According to some embodiments of the invention, the disulfide bond is an intermolecular disulfide bond formed between the Cys residues.

According to some embodiments of the invention, the multimeric peptide further comprises a Gly residue connecting the Cys residue to the carboxy end of the at least two peptide monomers.

According to some embodiments of the invention, each of the two at least two peptide monomers comprises the sequence selected from the group consisting of SEQ ID NOs: 2-7.

According to some embodiments of the invention, each of the at least two peptide monomers consists of the sequence selected from the group consisting of SEQ ID NOs: 8-13.

According to some embodiments of the invention, the multimeric peptide comprises at least one synthetic amino acid.

According to some embodiments of the invention, the at least two peptide monomers comprises least three peptide monomers.

According to some embodiments of the invention, the at least two peptide monomers are covalently linked to one another.

According to some embodiments of the invention, the disease is cancer.

According to some embodiments of the invention, the cancer of the subject expresses at least one HLA class I allele which is identical to a HLA class I allele expressed on cancer cells used to generate the cytotoxic T cells.

According to some embodiments of the invention, when the cancer cells are MCF-7, the cancer of the subject is selected from the group consisting of breast cancer, colon cancer, lung cancer and renal cancer.

According to some embodiments of the invention, the breast cancer comprises triple negative breast cancer.

According to some embodiments of the invention, the cytotoxic T cell line is generated using PBMCs.

According to some embodiments of the invention, the PBMCs are autologous to the subject.

According to some embodiments of the invention, the cancer of the subject is selected from the group consisting of breast cancer, colon cancer, lung cancer, Hodgkin's lymphoma, non-Hodgkin's lymphoma, acute lymphatic leukemia (ALL) and renal cancer.

According to some embodiments of the invention, the breast cancer comprises triple negative breast cancer.

According to some embodiments of the invention, the cytotoxic T cell line is generated by incubating T cells with pathogenic cells in the presence of a multimeric peptide comprising at least two peptide monomers linked to one another, each of the at least two peptide monomers comprising at least 6 consecutive amino acids from the amino acid sequence as set forth in SEQ ID NO: 1, wherein the at least two peptide monomers are each no longer than 30 amino acids, wherein the multimeric peptide is capable of reducing binding of PLIF to human leukocytes under conditions which allow expansion of the T cells.

According to some embodiments of the invention, the pathogenic cells are derived from the subject.

According to some embodiments of the invention, the pathogenic cells are not derived from the subject.

According to some embodiments of the invention, the cytotoxic T cell line is for treating a disease caused by a pathogenic cell population amenable to cytotoxic T cell therapy.

According to some embodiments of the invention, the disease is cancer.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a flow chart illustrating the generation of specific anti-breast cancer cytotoxic T cell lines.

FIGS. 2A-C are photomicrographs illustrating the effect of 5 day incubation of C24D peptide on T47D tumor cytolysis in the presence of peripheral blood mononuclear cells (PBMC).

FIGS. 3A-C are photomicrographs illustrating the effect of 7 day incubation of C24D peptide on T47D tumor cytolysis in the presence of peripheral blood mononuclear cells (PBMC).

FIGS. 4A-C are photomicrographs illustrating the effect of 5 day incubation of C24D peptide on MCF7 tumor cytolysis in the presence of peripheral blood mononuclear cells (PBMC).

FIGS. 5A-C are photomicrographs illustrating the effect of 7 day incubation of C24D peptide on MCF7 tumor cytolysis in the presence of peripheral blood mononuclear cells (PBMC).

Figure 6:
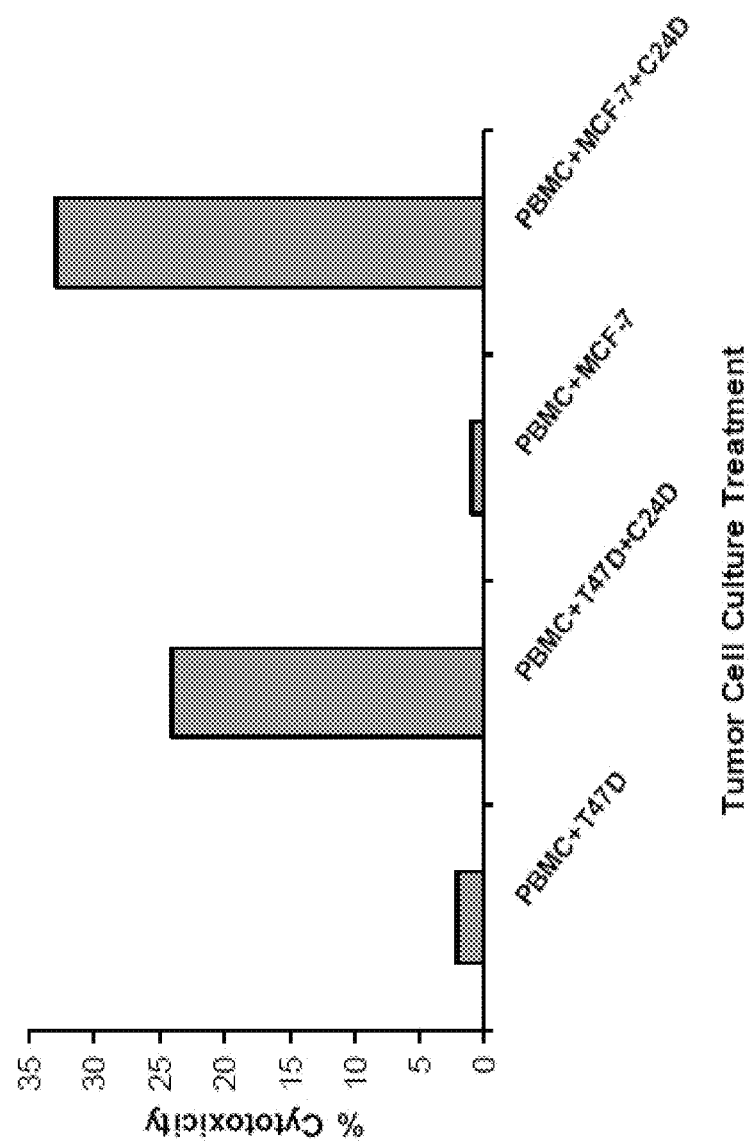

FIG. 6 is a bar graph illustrating the effect of C24D treatment on T47D and MCF7 tumor cell cytolysis by PBMC in culture (6 days).

Figure 7:
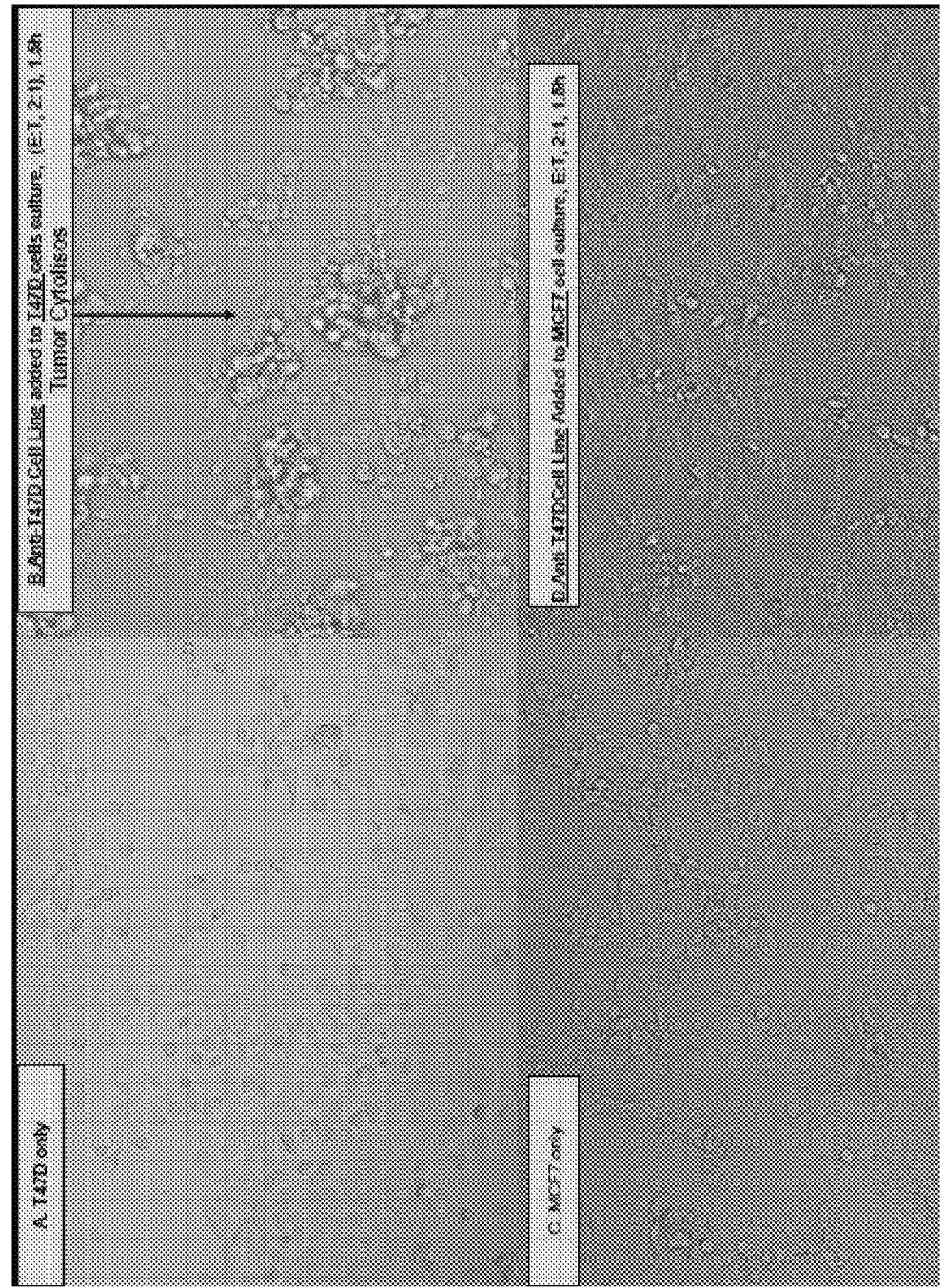

FIGS. 7A-D are photomicrographs illustrating the effect of 1.5 hours of culture of the anti-T47D cell line on T47D cells (FIG. 7B) and MCF7 cells (FIG. 7D).

Figure 8:
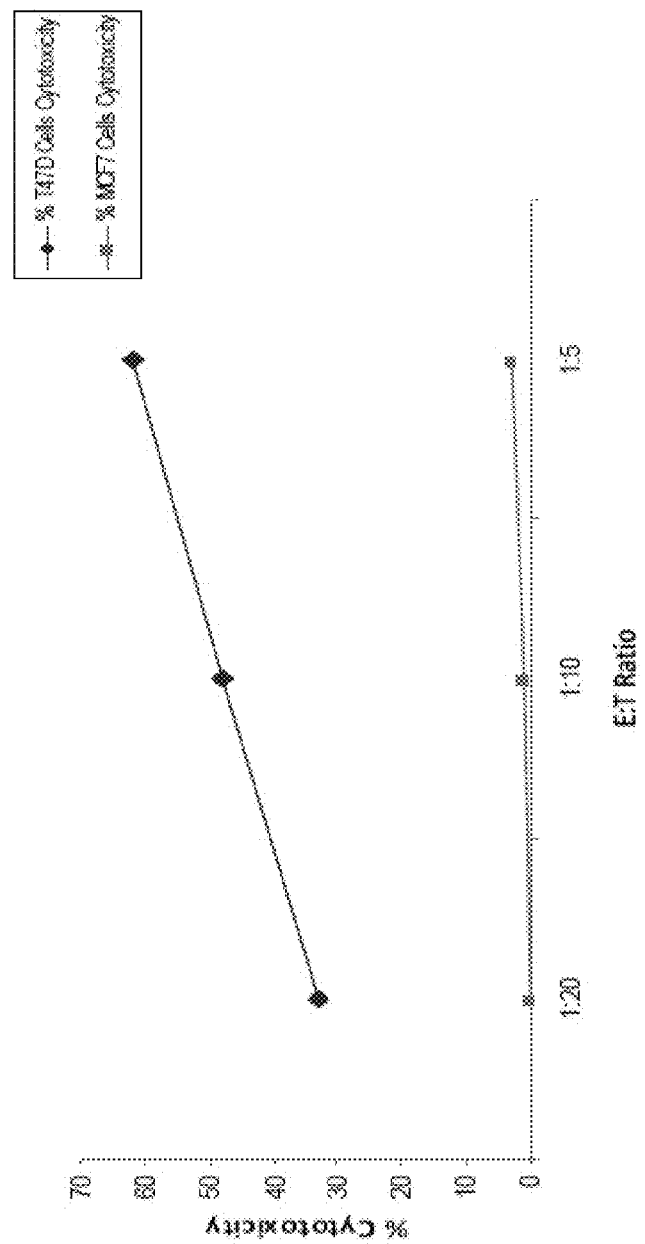

FIG. 8 is a graph illustrating the effect of 1.5 hours of culture of the anti-T47D cell line on T47D cells (blue) and MCF7 cells (pink).

Figure 9:
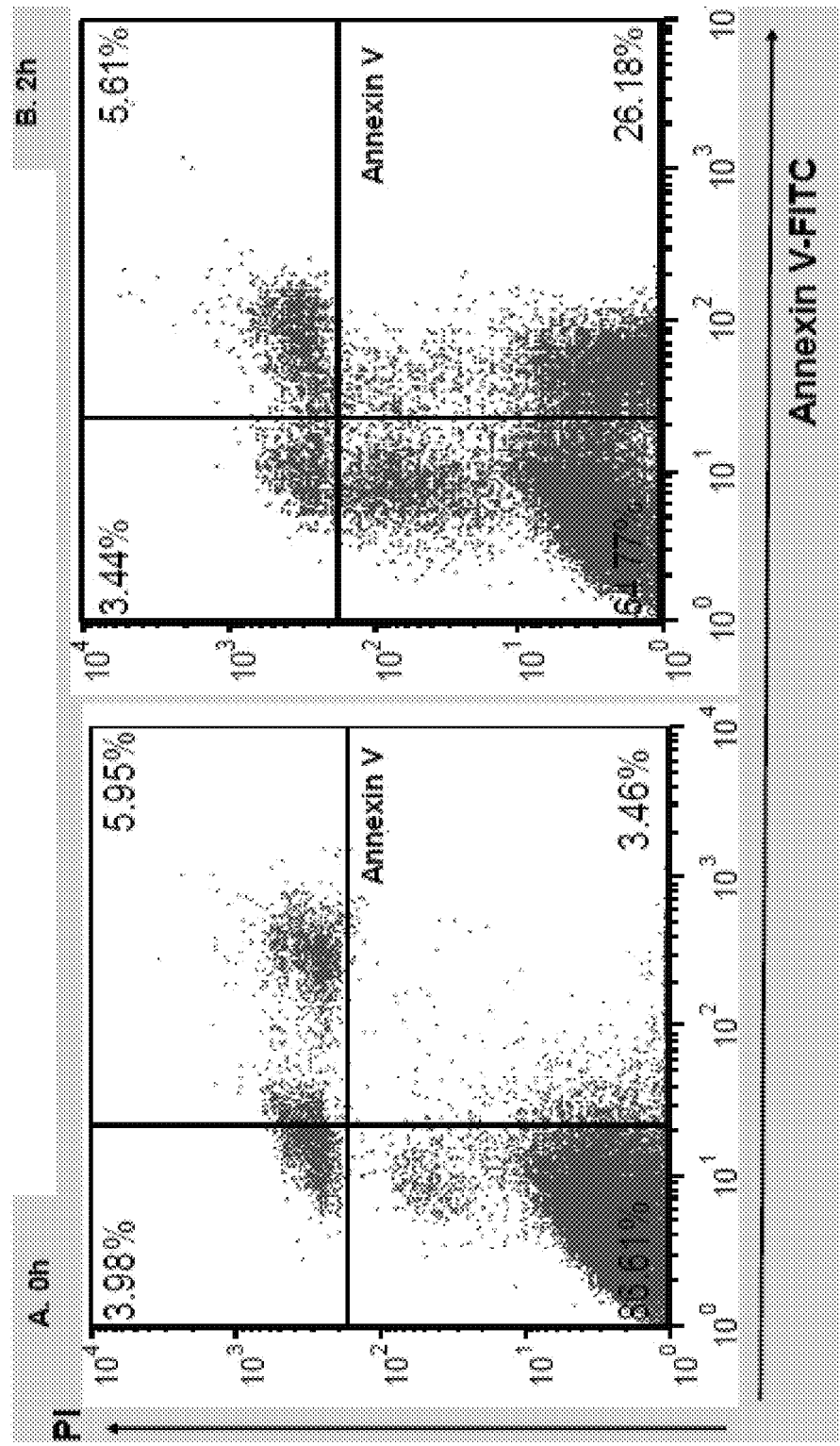

FIGS. 9A-B are graphs illustrating the results of FACS analysis analyzing apoptotosis of T47D Tumor Cells by the Specific CTL. Tumor Cells were cultured with anti-T47D CTL, for 0 h and 2 h, at E:T ratio 1:3. Cells were labeled with FITC Annexin V and PI.

Figure 10:
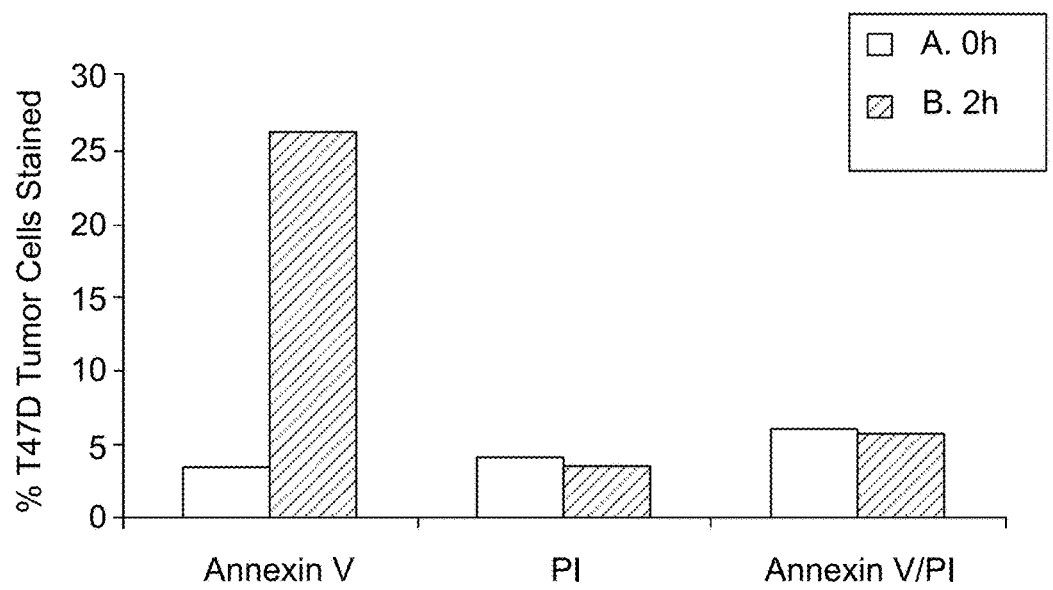

FIG. 10 is a graph illustrating that anti-T47D CTL induced early apoptosis as estimated by measurement of annexin V.

FIGS. 11A-D are photomicrographs of MDA-MB231 tumor cell cytolysis by anti-MCF7 CTL. A, C. Control MDA-MB231 target cells incubated with non-CTL PBMC. B. Cytolysis following incubation with HLA-A*0201+ identical anti-MCF7 CTL. D. No cytolysis with anti-HLA-A2-T47D CTL.

Figure 12:
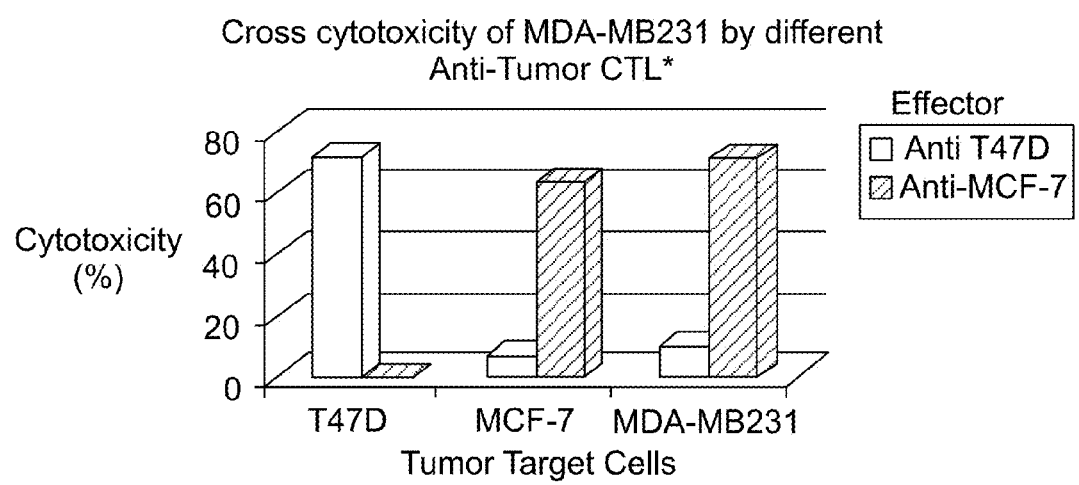

FIG. 12 is a graph illustrating the cross cytotoxicity of MDA-MB231 by different anti-tumor CTL as measured by MTT viability assay. Note the cytotoxicity of MDA-MB231 target treated with anti-MCF7 CTL compared to anti-T47D CTL.

Each value represents the mean from triplicate wells of the 3 experiments performed. Effector target ratio 1:1; 5 hours incubation at 37° C.

Figure 13:
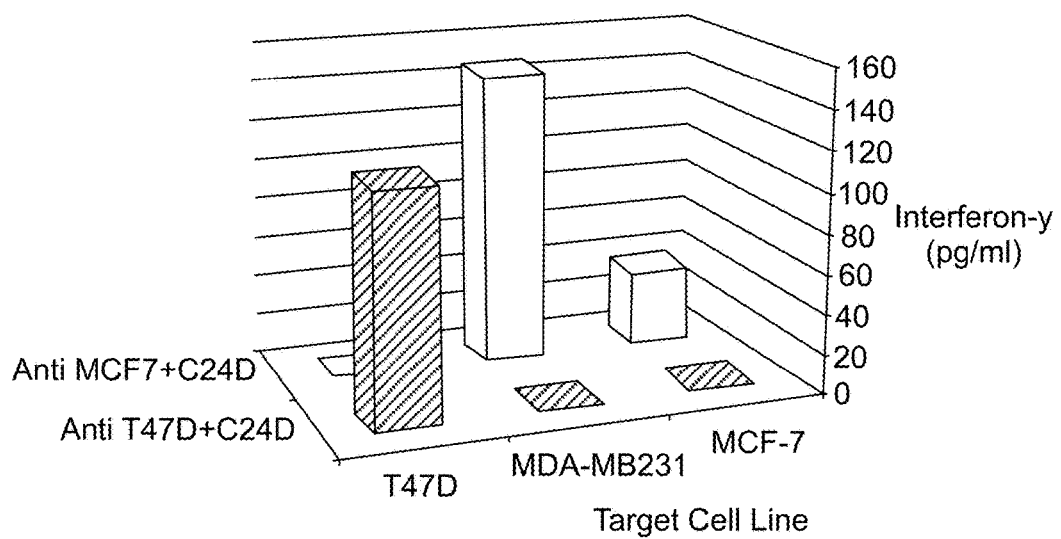

FIG. 13 is a graph illustrating the level of interferon-γ secretion by CTL following re-stimulation with MCF7, MDA-MB231 and T47D, indicating antigenic cross reactivity. Effector target ratio 1:1; 5 hours incubation at 37° C.

Figure 14:
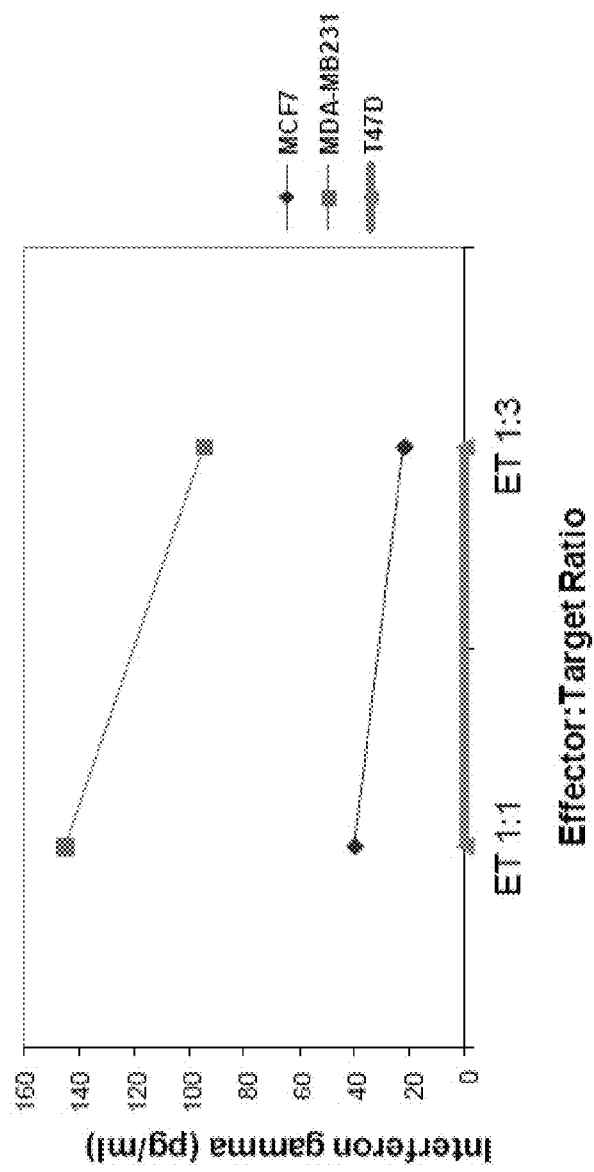

FIG. 14 is a graph illustrating interferon-γ secretion by anti-MCF7 CTL re-stimulated with MDA-MB231 and MCF-7. Effector target ratio 1:1 and 1:3; 5 hours incubation at 37° C.

DESCRIPTION OF SPECIFIC EMBODIMENTS OF THE INVENTION

The present invention, in some embodiments thereof, relates to generation of cytotoxic tumor specific cell lines using Placental Immunoregulatory Ferritin (PLIF) peptides.

Before explaining at least one embodiment of the invention in detail, it is to be understood that the invention is not necessarily limited in its application to the details set forth in the following description or exemplified by the Examples.

The invention is capable of other embodiments or of being practiced or carried out in various ways.

Tumor-specific cytotoxic lymphocytes have been proposed as a therapeutic for the treatment of cancer. They are usually expanded from peripheral blood mononuclear cells (PBMC) taken from tumor-bearing patients using antigen-presenting cells pulsed with irradiated tumor cells, tumor peptides, tumor lysates or fused tumor cells. This results in the expansion of MHC class I-restricted cytotoxic T cell lines over several weeks of culture. Tumor-specific cytotoxic T cell lines can also be derived as a subpopulation of tumor-infiltrating lymphocytes by modifying the methodologies, including a purification step based on the selection of CD8 T cells.

In human clinical trials, infusion of tumor-specific T cells derived from tumor-infiltrating lymphocytes or draining lymph nodes has shown limited but encouraging clinical responses in specific settings. Unfortunately, the ability to expand tumor antigen-specific T cells ex vivo from cancer patients is technically difficult due to numerous obstacles, including initiating cultures with low numbers of tumor-specific T cells and the physical inability to obtain tumor-infiltrating lymphocytes from patients with the most common malignancies.

Since Placenta Immunomodulatory Factor (PLIF) is a protein which is known to induce immune tolerance to certain malignant cells, the present inventors propose that an agent which blocks the activity of PLIF may allow for the activation of tumor specific T cells.

Whilst reducing the present invention to practice the present inventors showed that it was possible to generate cytotoxic T cells by incubating T cells with cancer cells in the presence of the PLIF antagonist C24D (FIGS. 2A-C-FIGS. 5A-C). Generation of T cell lines from these activated cells was effected using the expansion agent, interleukin 2. These cell lines were shown to be both cytotoxic and tumor specific (FIGS. 7A-D).

The present inventors further showed that T cells activated using one type of cancer cell were cytotoxic against another cancer cell provided that they shared HLA class I alleles. More specifically, the present inventors showed that T cells activated using the MCF7 breast cancer cell line were cytotoxic against MDA-MB231 cells (a breast cancer triple negative cell line (FIGS. 11A-D and FIG. 12). Both of these breast cancer cell lines express HLA*0201 peptide on their surface.

Accordingly, the present inventors propose the use of allogeneic HLA-A2-matched tumor cells as stimulator cells together with a PLIF antagonist for the generation of cytotoxic T cells, thereby expanding their potential for treating alloreactive tumors.

Thus, according to one aspect of the present invention there is provided an in-vitro method of activating T cells, the method comprising incubating T cells with pathogenic cells in the presence of a multimeric peptide comprising at least two peptide monomers linked to one another, each of the at least two peptide monomers comprising at least 6 consecutive amino acids from the amino acid sequence as set forth in SEQ ID NO: 1, wherein the at least two peptide monomers are each no longer than 30 amino acids, wherein the multimeric peptide is capable of reducing binding of PLIF to human leukocytes under conditions which allow expansion of the T cells.

As used herein, the phrase "An in-vitro method" refers to a method that does not occur within an animal. It will be appreciated that the term "in-vitro" may include the term "ex vivo", wherein at least one of the components of the incubation culture are derived from an animal.

The various components of the incubation reaction are discussed herein below:

T Cells

The term "T cells" refers to cytotoxic T cells. Cytotoxic T cells typically express a T cell receptor that binds to a specific antigen on the target cell.

The T cells may be derived from any mammalian species, such as human and may be obtained from white blood cell preparations or peripheral blood mononuclear cells (PBMCs) derived from a subject.

Alternatively, the T cells may have migrated into the tumor (i.e. may be comprised in tumor-infiltrating lymphocytes). Tumor infiltrating lymphocytes (TILs) can be isolated from an individual (e.g. during a tumor biopsy) and cultured in vitro (Kawakami, Y. et al. (1989) J. Immunol. 142: 2453-3461). An exemplary method for obtaining TILs includes plating viable cells (e.g. $1\times10^6$) of a single-cell suspension of enzymatically digested explant of metastatic tumor. It will be appreciated that the TILs may be isolated from fresh tumors or from frozen tissue (at the cost of lower yield).

The T cells are typically comprised in a heterogeneous population of white blood cells which includes antigen presenting cells and macrophages.

As mentioned, the T cells may be derived from PBMCs. PBMCs may be prepared as follows: Buffy coats from blood bank donors are layered onto Lymphoprep solution (Nycomed, Oslo, Norway) and spun at 2000 rpm for about 20 minutes. The interface layer is collected, washed, counted, and resuspended in PBS; pH 7.4 to the desired cell concentration.

Pathogenic Cells:

Contemplated pathogenic cells include any cells that comprise antigenic determinants on their surface. The pathogenic cells may be bacterial, fungal or viral. The pathogenic cells may be cells damaged by environmental factors such as ultraviolet light and other radiations. Alternatively, the pathogenic cells may be diseased cells such as cancer cells.

According to one embodiment the pathogenic cells are associated with an upregulated amount of Placenta Immunomodulatory Factor (PLIF). Such cells include lymphocytes from Hodgkin's and non-Hodgkin's lymphoma, acute lymphatic leukemia (ALL), cells from human breast cancer tissues and cells from breast cancer cell lines (e.g. T47D and MCF-7).

As used herein, the term "upregulated" refers to an increased amount of PLIF as compared to healthy cells of the same kind as the pathogenic cells. Thus, for example, if the pathogenic cells comprise lymphocytes, the amount of PLIF is upregulated as compared to the amount of PLIF in healthy lymphoctyes. As another example, if the pathogenic cells comprise breast cancer cells, the amount of PLIF is upregulated as compared to the amount of PLIF in healthy breast tissue.

The pathogenic cells may be obtained from a patient (e.g. during a biopsy) or may be available as a cell line.

Multimeric Peptide

The phrase "multimeric peptide" as used herein, describes a peptide formed from two or more peptide monomers (i.e. two or more peptide chains) that are associated covalently or non-covalently, with or without linkers. It will be appreciated that the peptide monomers are not linked together so as to form an amide bond through the amine group of one monomer and the carboxylic acid group of the other monomer so as to form a single extended chain.

According to a particular embodiment, the multimeric peptide is a dimer (i.e. comprises two peptide monomers that are associated covalently or non-covalently, with or without linkers). According to a particular embodiment, the two peptide monomers are not linked via a peptide bond.

The multimeric peptides disclosed herein are capable of blocking binding of PLIF to its receptor on white blood cells, thereby acting as an antagonist to the endogenous activity of Placenta Immunomodulatory Factor (PLIF).

PLIF is a protein composed of 165 amino acids. Of these, 117 match the ferritin heavy chain sequence, whereas the C-terminal 48 amino acids (C48) has a sequence which is not related to ferritin. It has been shown that the subcloned recombinant C48 peptide exhibits the bioactivity and therapeutic properties of PLIF [Moroz et al, J. Biol. Chem. 2002, 277, 12901-12905].

Methods of ascertaining whether the peptides are capable of antagonizing PLIF are known in the art and include for example analyzing the amount of each peptide that is capable of binding to white blood cells (leukocytes) both separately and/or in the same culture.

Binding affinity can be measured by any assay known or available to those skilled in the art, including but not limited to BIAcore measurements, ELISA assays, competition assays, etc. Bioactivity can be measured in vivo or in vitro by any assay known or available to those skilled in the art.

According to one embodiment, binding is measured using an antibody which is capable of specifically recognizing the peptides disclosed herein (i.e. binds with a higher affinity to the multimeric peptides disclosed herein than for C48 (SEQ ID NO: 100) or PLIF under identical conditions). Such antibodies are further described herein below.

The multimeric peptides of this aspect of the present invention typically comprise additional functions such as being capable of increasing interferon gamma (INF-γ) secretion and/or interleukin-10 (IL-10) secretion from activated leukocytes.

According to one embodiment, secretion of INF-γ is increased by at least two fold, or more preferably by at least five fold the amount of INF-γ that is basally secreted from activated leukocytes (i.e. in the absence of the disclosed peptides).

Methods of analyzing INF-γ secretion include but are not limited to ELISA kits such as those available from DPC, and R&D Systems, USA.

In some embodiments, the multimeric peptide is such that the amino acid sequence of each of its monomers are the same, thus forming a homomultimeric peptide. When the multimeric peptide is a dimer and the two monomers are identical, a homodimeric peptide is formed.

In some embodiments, the multimeric peptide is such that the amino acid sequence of at least two of its peptide monomers are different, thus forming a heteromultimeric peptide. When the multimeric peptide is a dimer and the two monomers are different, a heterodimeric peptide is formed.

As mentioned, the monomers of the multimeric peptide of this aspect of the present invention are derived from the C terminal amino acids of Placenta Immunomodulatory Factor (PLIF) and include at least 6 consecutive amino acids from the sequence as set forth in SEQ ID NO: 1 (His-His-Leu-Leu-Arg-Pro-Arg-Arg-Lys-Arg-Pro-His-Ser-Ile-Pro-Thr-Pro-Ile-Leu-Ile-Phe-Arg-Ser-Pro).

According to some embodiments, each monomer of the multimeric peptide comprises at least 7 consecutive amino acids from the sequence as set forth in SEQ ID NO: 1.

According to some embodiments, each monomer of the multimeric peptide comprises at least 8 consecutive amino acids from the sequence as set forth in SEQ ID NO: 1.

According to some embodiments, each monomer of the multimeric peptide comprises at least 9 consecutive amino acids from the sequence as set forth in SEQ ID NO: 1.

According to some embodiments, each monomer of the multimeric peptide comprises at least 10 consecutive amino acids from the sequence as set forth in SEQ ID NO: 1.

According to some embodiments, each monomer of the multimeric peptide comprises at least 11 consecutive amino acids from the sequence as set forth in SEQ ID NO: 1.

According to some embodiments, each monomer of the multimeric peptide comprises at least 12 consecutive amino acids from the sequence as set forth in SEQ ID NO: 1.

According to some embodiments, each monomer of the multimeric peptide comprises at least 13 consecutive amino acids from the sequence as set forth in SEQ ID NO: 1.

According to some embodiments, each monomer of the multimeric peptide comprises at least 14 consecutive amino acids from the sequence as set forth in SEQ ID NO: 1.

According to some embodiments, each monomer of the multimeric peptide comprises at least 15 consecutive amino acids from the sequence as set forth in SEQ ID NO: 1.

According to some embodiments, each monomer of the multimeric peptide comprises at least 16 consecutive amino acids from the sequence as set forth in SEQ ID NO: 1.

According to some embodiments, each monomer of the multimeric peptide comprises at least 17 consecutive amino acids from the sequence as set forth in SEQ ID NO: 1.

According to some embodiments, each monomer of the multimeric peptide comprises at least 18 consecutive amino acids from the sequence as set forth in SEQ ID NO: 1.

According to some embodiments, each monomer of the multimeric peptide comprises at least 19 consecutive amino acids from the sequence as set forth in SEQ ID NO: 1.

According to some embodiments, each monomer of the multimeric peptide comprises at least 20 consecutive amino acids from the sequence as set forth in SEQ ID NO: 1.

According to some embodiments, each monomer of the multimeric peptide comprises at least 21 consecutive amino acids from the sequence as set forth in SEQ ID NO: 1.

According to some embodiments, each monomer of the multimeric peptide comprises at least 22 consecutive amino acids from the sequence as set forth in SEQ ID NO: 1.

According to some embodiments, each monomer of the multimeric peptide comprises at least 23 consecutive amino acids from the sequence as set forth in SEQ ID NO: 1.

According to some embodiments, each monomer of the multimeric peptide comprises the full length sequence as set forth in SEQ ID NO: 1.

According to a particular embodiment the amino acid sequence derived from SEQ ID NO: 1 is HSIPTPILIFRSP (SEQ ID NO: 2), HLLRPRRRKRPHSI (SEQ ID NO: 3), RPRRRKRPHSIP (SEQ ID NO: 4), SIPTPILIFRSP (SEQ ID NO: 5), PHSIPTPILIFRSP (SEQ ID NO: 6) or HHLL-RPRRRKR (SEQ ID NO: 7).

Preferably, each monomer of the multimeric peptide comprises at least 6, at least 7, at least 8, at least 9, at least 10, at least 11, at least 12, at least 13, at least 14 consecutive amino acids from the sequence as set forth in SEQ ID NO: 14-RPHSIPTPILIFRSP.

Additional contemplated peptides include those set forth in Table 1, herein below.

TABLE 1

| SEQ ID | Sequence |
|---|---|
| 15 | His-His-Leu-Leu-Arg-Pro |
| 16 | His-Leu-Leu-Arg-Pro-Arg |
| 17 | Leu-Leu-Arg-Pro-Arg-Arg |
| 18 | Leu-Arg-Pro-Arg-Arg-Lys |
| 19 | Arg-Pro-Arg-Arg-Lys-Arg |
| 20 | Pro-Arg-Arg-Lys-Arg-Pro |
| 21 | Arg-Arg-Lys-Arg-Pro-His |
| 22 | Arg-Lys-Arg-Pro-His-Ser |
| 23 | Lys-Arg-Pro-His-Ser-Ile |
| 24 | Arg-Pro-His-Ser-Ile-Pro |
| 25 | Pro-His-Ser-Ile-Pro-Thr |
| 26 | His-Ser-Ile-Pro-Thr-Pro |
| 27 | Ser-Ile-Pro-Thr-Pro-Ile |
| 28 | Ile-Pro-Thr-Pro-Ile-Leu |
| 29 | Pro-Thr-Pro-Ile-Leu-Ile |
| 30 | Thr-Pro-Ile-Leu-Ile-Phe |
| 31 | Pro-Ile-Leu-Ile-Phe-Arg |
| 32 | Ile-Leu-Ile-Phe-Arg-Ser |
| 33 | Leu-Ile-Phe-Arg-Ser-Pro |
| 34 | His-His-Leu-Leu-Arg-Pro-Arg |
| 35 | His-Leu-Leu-Arg-Pro-Arg-Arg |
| 36 | Leu-Leu-Arg-Pro-Arg-Arg-Lys |
| 37 | Leu-Arg-Pro-Arg-Arg-Lys-Arg |
| 38 | Arg-Pro-Arg-Arg-Lys-Arg-Pro |
| 39 | Pro-Arg-Arg-Lys-Arg-Pro-His |
| 40 | Arg-Arg-Lys-Arg-Pro-His-Ser |
| 41 | Arg-Lys-Arg-Pro-His-Ser-Ile |
| 42 | Lys-Arg-Pro-His-Ser-Ile-Pro |
| 43 | Arg-Pro-His-Ser-Ile-Pro-Thr |
| 44 | Pro-His-Ser-Ile-Pro-Thr-Pro |
| 45 | His-Ser-Ile-Pro-Thr-Pro-Ile |
| 46 | Ser-Ile-Pro-Thr-Pro-Ile-Leu |
| 47 | Ile-Pro-Thr-Pro-Ile-Leu-Ile |
| 48 | Pro-Thr-Pro-Ile-Leu-Ile-Phe |
| 49 | Thr-Pro-Ile-Leu-Ile-Phe-Arg |
| 50 | Pro-Ile-Leu-Ile-Phe-Arg-Ser |
| 51 | Ile-Leu-Ile-Phe-Arg-Ser-Pro |
| 52 | His-His-Leu-Leu-Arg-Pro-Arg-Arg |
| 53 | His-Leu-Leu-Arg-Pro-Arg-Arg-Lys |
| 54 | Leu-Leu-Arg-Pro-Arg-Arg-Lys-Arg |
| 55 | Leu-Arg-Pro-Arg-Arg-Lys-Arg-Pro |
| 56 | Arg-Pro-Arg-Arg-Lys-Arg-Pro-His |
| 57 | Pro-Arg-Arg-Lys-Arg-Pro-His-Ser |
| 58 | Arg-Arg-Lys-Arg-Pro-His-Ser-Ile |
| 59 | Arg-Lys-Arg-Pro-His-Ser-Ile-Pro |
| 60 | Lys-Arg-Pro-His-Ser-Ile-Pro-Thr |
| 61 | Arg-Pro-His-Ser-Ile-Pro-Thr-Pro |
| 62 | Pro-His-Ser-Ile-Pro-Thr-Pro-Ile |
| 63 | His-Ser-Ile-Pro-Thr-Pro-Ile-Leu |
| 64 | Ser-Ile-Pro-Thr-Pro-Ile-Leu-Ile |
| 65 | Ile-Pro-Thr-Pro-Ile-Leu-Ile-Phe |
| 66 | Pro-Thr-Pro-Ile-Leu-Ile-Phe-Arg |
| 67 | Thr-Pro-Ile-Leu-Ile-Phe-Arg-Ser |
| 68 | Pro-Ile-Leu-Ile-Phe-Arg-Ser-Pro |
| 69 | His-His-Leu-Leu-Arg-Pro-Arg-Arg-Lys |
| 70 | His-Leu-Leu-Arg-Pro-Arg-Arg-Lys-Arg |
| 71 | Leu-Leu-Arg-Pro-Arg-Arg-Lys-Arg-Pro |
| 72 | Leu-Arg-Pro-Arg-Arg-Lys-Arg-Pro-His |
| 73 | Arg-Pro-Arg-Arg-Lys-Arg-Pro-His-Ser |
| 74 | Pro-Arg-Arg-Lys-Arg-Pro-His-Ser-Ile |
| 75 | Arg-Arg-Lys-Arg-Pro-His-Ser-Ile-Pro |
| 76 | Arg-Lys-Arg-Pro-His-Ser-Ile-Pro-Thr |
| 77 | Lys-Arg-Pro-His-Ser-Ile-Pro-Thr-Pro |
| 78 | Arg-Pro-His-Ser-Ile-Pro-Thr-Pro-Ile |
| 79 | Pro-His-Ser-Ile-Pro-Thr-Pro-He-Leu |
| 80 | His-Ser-Ile-Pro-Thr-Pro-Ile-Leu-Ile |
| 81 | Ser-Ile-Pro-Thr-Pro-Ile-Leu-Ile-Phe |
| 82 | Ile-Pro-Thr-Pro-Ile-Leu-Ile-Phe-Arg |
| 83 | Pro-Thr-Pro-Ile-Leu-Ile-Phe-Arg-Ser |
| 84 | Thr-Pro-Ile-Leu-Ile-Phe-Arg-Ser-Pro |
| 85 | His-His-Leu-Leu-Arg-Pro-Arg-Arg-Lys-Arg |
| 86 | His-Leu-Leu-Arg-Pro-Arg-Arg-Lys-Arg-Pro |
| 87 | Leu-Leu-Arg-Pro-Arg-Arg-Lys-Arg-Pro-His |
| 88 | Leu-Arg-Pro-Arg-Arg-Lys-Arg-Pro-His-Ser |
| 89 | Arg-Pro-Arg-Arg-Lys-Arg-Pro-His-Ser-Ile |
| 90 | Pro-Arg-Arg-Lys-Arg-Pro-His-Ser-Ile-Pro |
| 91 | Arg-Arg-Lys-Arg-Pro-His-Ser-Ile-Pro-Thr |
| 92 | Arg-Lys-Arg-Pro-His-Ser-He-Pro-Thr-Pro |

TABLE 1-continued

| SEQ ID | Sequence |
|---|---|
| 93 | Lys-Arg-Pro-His-Ser-Ile-Pro-Thr-Pro-He |
| 94 | Arg-Pro-His-Ser-Ile-Pro-Thr-Pro-Ile-Leu |
| 95 | Pro-His-Ser-Ile-Pro-Thr-Pro-He-Leu-He |
| 96 | His-Ser-Ile-Pro-Thr-Pro-Ile-Leu-Ile-Phe |
| 97 | Ser-Ile-Pro-Thr-Pro-Ile-Leu-Ile-Phe-Arg |
| 98 | Ile-Pro-Thr-Pro-Ile-Leu-Ile-Phe-Arg-Ser |
| 99 | Pro-Thr-Pro-Ile-Leu-Ile-Phe-Arg-Ser-Pro |

The term "peptide" as used herein refers to a polymer of natural or synthetic amino acids, encompassing native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides even more stable while in a body or more capable of penetrating into cells.

Such modifications include, but are not limited to N terminus modification, C terminus modification, peptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated bonds (—N(CH3)-CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2), thioamide bonds (—CS—NH—), olefinic double bonds (—CH=CH—), retro amide bonds (—NH—CO—), peptide derivatives (—N(R)—CH2-CO—), wherein R is the "normal" side chain, naturally presented on the carbon atom.

These modifications can occur at any of the bonds along the peptide chain and even at several (2-3) at the same time.

Natural aromatic amino acids, Trp, Tyr and Phe, may be substituted for synthetic non-natural acid such as Phenylglycine, TIC, naphthylelanine (Nol), ring-methylated derivatives of Phe, halogenated derivatives of Phe or o-methyl-Tyr.

In addition to the above, the peptides of the present invention may also include one or more modified amino acids or one or more non-amino acid monomers (e.g. fatty acids, complex carbohydrates etc).

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodemosine, nor-valine, nor-leucine and ornithine. Furthermore, the term "amino acid" includes both D- and L-amino acids (stereoisomers).

Tables 2 and 3 below list naturally occurring amino acids (Table 2) and non-conventional or modified amino acids (Table 3) which can be used with the present invention.

TABLE 2

| One-letter Symbol | Three-Letter Abbreviation | Amino Acid |
|---|---|---|
| A | Ala | alanine |
| R | Arg | Arginine |
| N | Asn | Asparagine |
| D | Asp | Aspartic acid |
| C | Cys | Cysteine |
| Q | Gln | Glutamine |
| E | Glu | Glutamic Acid |
| G | Gly | glycine |
| H | His | Histidine |
| I | Iie | isoleucine |
| L | Leu | leucine |
| K | Lys | Lysine |
| M | Met | Methionine |
| F | Phe | phenylalanine |
| P | Pro | Proline |
| S | Ser | Serine |
| T | Thr | Threonine |
| W | Trp | tryptophan |
| Y | Tyr | tyrosine |
| V | Val | Valine |
| X | Xaa | Any amino acid as above |

TABLE 3

| Code | Non-conventional amino acid | Code | Non-conventional amino acid |
|---|---|---|---|
| Nmala | L-N-methylalanine | Abu | α-aminobutyric acid |
| Nmarg | L-N-methylarginine | Mgabu | α-amino-α-methylbutyrate |
| Nmasn | L-N-methylasparagine | Cpro | aminocyclopropane-carboxylate |
| Nmasp | L-N-methylaspartic acid | | |
| Nmcys | L-N-methylcysteine | Aib | aminoisobutyric acid |
| Nmgin | L-N-methylglutamine | Norb | aminonorbornyl-carboxylate |
| Nmglu | L-N-methylglutamic acid | | |
| Nmhis | L-N-methylhistidine | Chexa | cyclohexylalanine |
| Nmile | L-N-methylisolleucine | Cpen | cyclopentylalanine |
| Nmleu | L-N-methylleucine | Dal | D-alanine |
| Nmlys | L-N-methyllysine | Darg | D-arginine |
| Nmmet | L-N-methylmethionine | Dasp | D-aspartic acid |
| Nmnle | L-N-methylnorleucine | Dcys | D-cysteine |
| Nmnva | L-N-methylnorvaline | Dgln | D-glutamine |
| Nmorn | L-N-methylornithine | Dglu | D-glutamic acid |
| Nmphe | L-N-methylphenylalanine | Dhis | D-histidine |
| Nmpro | L-N-methylproline | Dile | D-isoleucine |
| Nmser | L-N-methylserine | Dleu | D-leucine |

TABLE 3-continued

| Code | Non-conventional amino acid | Code | Non-conventional amino acid |
| --- | --- | --- | --- |
| Nmthr | L-N-methylthreonine | Dlys | D-lysine |
| Nmtrp | L-N-methyltryptophan | Dmet | D-methionine |
| Nmtyr | L-N-methyltyrosine | Dorn | D-ornithine |
| Nmval | L-N-methylvaline | Dphe | D-phenylalanine |
| Nmetg | L-N-methylethylglycine | Dpro | D-proline |
| Nmtbug | L-N-methyl-t-butylglycine | Dser | D-serine |
| Nle | L-norleucine | Dthr | D-threonine |
| Nva | L-norvaline | Dtrp | D-tryptophan |
| Maib | α-methyl-aminoisobutyrate | Dtyr | D-tyrosine |
| Mgabu | α-methyl-γ-aminobutyrate | Dval | D-valine |
| Mchexa | α ethylcyclohexylalanine | Dmala | D-α-methylalanine |
| Mcpen | α-methylcyclopentylalanine | Dmarg | D-α-methylarginine |
| Manap | α-methyl-α-napthylalanine | Dmasn | D-α-methylasparagine |
| Mpen | α-methylpenicillamine | Dmasp | D-α-methylaspartate |
| Nglu | N-(4-aminobutyl)glycine | Dmcys | D-α-methylcysteine |
| Naeg | N-(2-aminoethyl)glycine | Dmgln | D-α-methylglutamine |
| Norn | N-(3-aminopropyl)glycine | Dmhis | D-α-methylhistidine |
| Nmaabu | N-amino-α-methylbutyrate | Dmile | D-α-methylisoleucine |
| Anap | α-napthylalanine | Dmleu | D-α-methylleucine |
| Nphe | N-benzylglycine | Dmlys | D-α-methyllysine |
| Ngln | N-(2-carbamylethyl)glycine | Dmmet | D-α-methylmethionine |
| Nasn | N-(carbamylmethyl)glycine | Dmorn | D-α-methylornithine |
| Nglu | N-(2-carboxyethyl)glycine | Dmphe | D-α-methylphenylalanine |
| Nasp | N-(carboxymethyl)glycine | Dmpro | D-α-methylproline |
| Ncbut | N-cyclobutylglycine | Dmser | D-α-methylserine |
| Nchep | N-cycloheptylglycine | Dmthr | D-α-methylthreonine |
| Nchex | N-cyclohexylglycine | Dmtrp | D-α-methyltryptophan |
| Ncdec | N-cyclodecylglycine | Dmty | D-α-methyltyrosine |
| Ncdod | N-cyclododeclglycine | Dmval | D-α-methylvaline |
| Ncoct | N-cyclooctylglycine | Dnmala | D-α-methylalnine |
| Ncpro | N-cyclopropylglycine | Dnmarg | D-α-methylarginine |
| Ncund | N-cycloundecylglycine | Dnmasn | D-α-methylasparagine |
| Nbhm | N-(2,2-diphenylethyl)glycine | Dnmasp | D-α-methylasparatate |
| Nbhe | N-(3,3-diphenylpropyl)glycine | Dnmcys | D-α-methylcysteine |
| Nhtrp | N-(3-indolylyethyl) glycine | Dnmleu | D-N-methylleucine |
| Nmgabu | N-methyl-γ-aminobutyrate | Dnmlys | D-N-methyllysine |
| Dnmmet | D-N-methylmethionine | Nmchexa | N-methylcyclohexylalanine |
| Nmcpen | N-methylcyclopentylalanine | Dnmorn | D-N-methylornithine |
| Dnmphe | D-N-methylphenylalanine | Nala | N-methylglycine |
| Dnmpro | D-N-methylproline | Nmaib | N-methylaminoisobutyrate |
| Dnmser | D-N-methylserine | Nile | N-(1-methylpropyl)glycine |
| Dnmser | D-N-methylserine | Nile | N-(2-methylpropyl)glycine |
| Dnmthr | D-N-methylthreonine | Nleu | N-(2-methylpropyl)glycine |
| Nva | N-(1-methylethyl)glycine | Dnmtrp | D-N-methyltryptophan |
| Nmanap | N-methyla-napthylalanine | Dnmtyr | D-N-methyltyrosine |
| Nmpen | N-methylpenicillamine | Dnmval | D-N-methylvaline |
| Nhtyr | N-(p-hydroxyphenyl)glycine | Gabu | γ-aminobutyric acid |
| Ncys | N-(thiomethyl)glycine | Tbug | L-t-butylglycine |
| Pen | penicillamine | Etg | L-ethylglycine |
| Mala | L-α-methylalanine | Hphe | L-homophenylalanine |
| Masn | L-α-methylasparagine | Marg | L-α-methylarginine |
| Mtbug | L-α-methyl-t-butylglycine | Masp | L-α-methylaspartate |
| Metg | L-methylethylglycine | Mcys | L-α-methylcysteine |
| Mglu | L-α-methylglutamate | Mgln | L-α thylglutamine |
| Mhphe | L-α-methylhomo phenylalanine | Mhis | L-α-methylhistidine |
| Nmet | N-(2-methylthioethyl)glycine | Mile | L-α-methylisoleucine |
| Narg | N-(3-guanidinopropyl)glycine | Dmgln | D-N-methylglutamine |
| Nthr | N-(1-hydroxyethyl)glycine | Dnmglu | D-N-methylglutamate |
| Nser | N-(hydroxyethyl)glycine | Dnmhis | D-N-methylhistidine |
| Nhis | N-(imidazolylethyl)glycine | Dnmile | D-N-methylisoleucine |
| Nhtrp | N-(3-indolylyethyl)glycine | Dnmleu | D-N-methylleucine |
| Nmgabu | N-methyl-γ-aminobutyrate | Dnmlys | D-N-methyllysine |
| Dnmmet | D-N-methylmethionine | Nmchexa | N-methylcyclohexylalanine |
| Nmcpen | N-methylcyclopentylalanine | Dnmorn | D-N-methylornithine |
| Dnmphe | D-N-methylphenylalanine | Nala | N-methylglycine |
| Dnmpro | D-N-methylproline | Nmaib | N-methylaminoisobutyrate |
| Dnmser | D-N-methylserine | Nile | N-(1-methylpropyl)glycine |
| Dnmthr | D-N-methylthreonine | Nleu | N-(2-methylpropyl)glycine |
| Nval | N-(1-methylethyl)glycine | Dnmtrp | D-N-methyltryptophan |
| Nmanap | N-methyla-napthylalanine | Dnmtyr | D-N-methyltyrosine |
| Nmpen | N-methylpenicillamine | Dnmval | D-N-methylvaline |
| Nhtyr | N-(p-hydroxyphenyl)glycine | Gabu | γ-aminobutyric acid |
| Ncys | N-(thiomethyl)glycine | Tbug | L-t-butylglycine |
| Pen | penicillamine | Etg | L-ethylglycine |
| Mala | L-α-methylalanine | Hphe | L-homophenylalanine |
| Masn | L-α-methylasparagine | Marg | L-α-methylarginine |

TABLE 3-continued

| Code | Non-conventional amino acid | Code | Non-conventional amino acid |
|---|---|---|---|
| Mtbug | L-α-methyl-t-butylglycine | Masp | L-α-methylaspartate |
| Metg | L-methylethylglycine | Mcys | L-α-methylcysteine |
| Mglu | L-α-methylglutamate | Mgln | L-α-methylglutamine |
| Mhphe | L-α-methylhomophenylalanine | Mhis | L-α ethylhistidine |
| Nmet | N-(2-methylthioethyl)glycine | Mile | L-α thylisoleucine |
| Mlys | L-α-methyllysine | Mleu | L-α-methylleucine |
| Mnle | L-α-methylnorleucine | Mmet | L-α-methylmethionine |
| Morn | L-α-methylornithine | Mnva | L-α-methylnorvaline |
| Mpro | L-α-methylproline | Mphe | L-α-methylphenylalanine |
| Mthr | L-α-methylthreonine | mser | L-α-methylserine |
| Mtyr | L-α-methyltyrosine | Mtrp | L-α ethylvaline |
| Nmhphe | L-N-methylhomophenylalanine | Mval | L-α-methylleucine |
| | N-(N-(3,3-diphenylpropyl) | Nnbhm | |
| Nnbhe | carbamylmethyl(1)glycine | Nnbhm | N-(N-(2,2-diphenylethyl) carbamylmethyl-glycine |
| | | Nmbc | 1-carboxy-1-(2,2-diphenyl ethylamino)cyclopropane |

It will be appreciated that additional peptides are contemplated by the present invention as well as those disclosed herein, which may be synthesized (comprising conservative or non-conservative substitutions) in order to "tweak" the peptides and generate PLIF-derived peptides with improved characteristics i.e. comprising an enhanced ability to block PLIF binding and/or to stimulate the secretion of IFN from T lymphocytes.

Thus, in other embodiments, the peptide monomers comprise a homolog, a variant, or a functional fragment of the sequences described herein above. In another embodiment, the peptide monomers comprise an amino acid sequence that is about 60%, 65%, 70%, 75%, 80%, 85%, 90%, or 95% identical to the sequences described herein above.

The term "conservative substitution" as used herein, refers to the replacement of an amino acid present in the native sequence in the peptide with a naturally or non-naturally occurring amino or a peptidomimetics having similar steric properties. Where the side-chain of the native amino acid to be replaced is either polar or hydrophobic, the conservative substitution should be with a naturally occurring amino acid, a non-naturally occurring amino acid or with a peptidomimetic moiety which is also polar or hydrophobic (in addition to having the same steric properties as the side-chain of the replaced amino acid).

As naturally occurring amino acids are typically grouped according to their properties, conservative substitutions by naturally occurring amino acids can be easily determined bearing in mind the fact that in accordance with the invention replacement of charged amino acids by sterically similar non-charged amino acids are considered as conservative substitutions.

For producing conservative substitutions by non-naturally occurring amino acids it is also possible to use amino acid analogs (synthetic amino acids) well known in the art. A peptidomimetic of the naturally occurring amino acid is well documented in the literature known to the skilled practitioner.

When affecting conservative substitutions the substituting amino acid should have the same or a similar functional group in the side chain as the original amino acid.

The phrase "non-conservative substitutions" as used herein refers to replacement of the amino acid as present in the parent sequence by another naturally or non-naturally occurring amino acid, having different electrochemical and/or steric properties. Thus, the side chain of the substituting amino acid can be significantly larger (or smaller) than the side chain of the native amino acid being substituted and/or can have functional groups with significantly different electronic properties than the amino acid being substituted. Examples of non-conservative substitutions of this type include the substitution of phenylalanine or cycohexylmethyl glycine for alanine, isoleucine for glycine, or —NH—CH[(—CH$_2$)$_5$—COOH]—CO— for aspartic acid. Those non-conservative substitutions which fall under the scope of the present invention are those which still constitute a peptide having anti-bacterial properties.

The N and C termini of the peptides of the present invention may be protected by function groups. Suitable functional groups are described in Green and Wuts, "Protecting Groups in Organic Synthesis", John Wiley and Sons, Chapters 5 and 7, 1991, the teachings of which are incorporated herein by reference.

Hydroxyl protecting groups include esters, carbonates and carbamate protecting groups. Amine protecting groups include alkoxy and aryloxy carbonyl groups, as described above for N-terminal protecting groups. Carboxylic acid protecting groups include aliphatic, benzylic and aryl esters, as described above for C-terminal protecting groups. In one embodiment, the carboxylic acid group in the side chain of one or more glutamic acid or aspartic acid residue in a peptide of the present invention is protected, preferably with a methyl, ethyl, benzyl or substituted benzyl ester.

Examples of N-terminal protecting groups include acyl groups (—CO—R1) and alkoxy carbonyl or aryloxy carbonyl groups (—CO—O—R1), wherein R1 is an aliphatic, substituted aliphatic, benzyl, substituted benzyl, aromatic or a substituted aromatic group. Specific examples of acyl groups include acetyl, (ethyl)-CO—, n-propyl-CO—, iso-propyl-CO—, n-butyl-CO—, sec-butyl-CO—, t-butyl-CO—, hexyl, lauroyl, palmitoyl, myristoyl, stearyl, oleoyl phenyl-CO—, substituted phenyl-CO—, benzyl-CO— and (substituted benzyl)-CO—. Examples of alkoxy carbonyl and aryloxy carbonyl groups include CH3-O—CO—, (ethyl)-O—CO—, n-propyl-O—CO—, iso-propyl-O—CO—, n-butyl-O—CO—, sec-butyl-O—CO—, t-butyl-O—CO—, phenyl-O—CO—, substituted phenyl-O—CO— and benzyl-O—CO—, (substituted benzyl)-O—CO—. Adamantan, naphtalen, myristoleyl, tuluen, biphenyl, cinnamoyl, nitrobenzoy, toluoyl, furoyl, benzoyl, cyclohexane, norbomane, Z-caproic. In order to facilitate the N-acylation, one to four glycine residues can be present in the N-terminus of the molecule.

The carboxyl group at the C-terminus of the compound can be protected, for example, by an amide (i.e., the hydroxyl group at the C-terminus is replaced with —NH$_2$, —NHR$_2$ and —NR$_2$R$_3$) or ester (i.e. the hydroxyl group at the C-terminus is replaced with —OR$_2$). R$_2$ and R$_3$ are independently an aliphatic, substituted aliphatic, benzyl, substituted benzyl, aryl or a substituted aryl group. In addition, taken together with the nitrogen atom, R$_2$ and R$_3$ can form a C4 to C8 heterocyclic ring with from about 0-2 additional heteroatoms such as nitrogen, oxygen or sulfur. Examples of suitable heterocyclic rings include piperidinyl, pyrrolidinyl, morpholino, thiomorpholino or piperazinyl. Examples of C-terminal protecting groups include —NH$_2$, —NHCH$_3$, —N(CH$_3$)$_2$, —NH(ethyl), —N(ethyl)$_2$, —N(methyl) (ethyl), —NH(benzyl), —N(C1-C4 alkyl) (benzyl), —NH(phenyl), —N(C1-C4 alkyl) (phenyl), —OCH$_3$, —O-(ethyl), —O-(n-propyl), —O-(n-butyl), —O-(iso-propyl), —O-(sec-butyl), —O-(t-butyl), —O-benzyl and —O-phenyl.

The peptides of the present invention may also comprise non-amino acid moieties, such as for example, hydrophobic moieties (various linear, branched, cyclic, polycyclic or hetrocyclic hydrocarbons and hydrocarbon derivatives) attached to the peptides; various protecting groups, especially where the compound is linear, which are attached to the compound's terminals to decrease degradation. Chemical (non-amino acid) groups present in the compound may be included in order to improve various physiological properties such; decreased degradation or clearance; decreased repulsion by various cellular pumps, improve immunogenic activities, improve various modes of administration (such as attachment of various sequences which allow penetration through various bathers, through the gut, etc.); increased specificity, increased affinity, decreased toxicity and the like.

Exemplary side chain protecting groups and their positioning are described in the Examples section herein below.

Linking of the monomers of the PLIF derived monomers may be effected using any method known in the art provided that the linking does not substantially interfere with the bioactivity of the multimeric peptide—e.g. to interfere with the ability of the multimeric peptide to block the binding of PLIF to receptors on leukocytes (e.g. T cells).

The monomers of this aspect of the present invention may be linked through a linking moiety.

Examples of linking moieties include but are not limited to a simple covalent bond, a flexible peptide linker, a disulfide bridge or a polymer such as polyethylene glycol (PEG). Peptide linkers may be entirely artificial (e.g., comprising 2 to 20 amino acid residues independently selected from the group consisting of glycine, serine, asparagine, threonine and alanine) or adopted from naturally occurring proteins. Disulfide bridge formation can be achieved, e.g., by addition of cysteine residues, as further described herein below. Linking through polyethylene glycols (PEG) can be achieved by reaction of monomers having free cysteines with multifunctional PEGs, such as linear bis-maleimide PEGs. Alternatively, linking can be performed though the glycans on the monomer after their oxidation to aldehyde form and using multifunctional PEGs containing aldehyde-reactive groups.

Selection of the position of the link between the two monomers should take into account that the link should not substantially interfere with the ability of the multimer to block the binding of PLIF to receptors on T cells.

Thus, for example, the linking moiety is optionally a moiety which is covalently attached to a side chain, an N-terminus or a C-terminus of the first peptide monomer, as well as to a side chain, an N-terminus or a C-terminus of the second peptide monomer.

Preferably the linking moiety is attached to the C-terminus of the first peptide monomer, and to the C-terminus of the second peptide monomer.

As mentioned, the linking moiety used in this aspect of the present invention may be a cysteine residue.

Thus, in some embodiments of the invention, each of the peptide monomers comprises an amino acid sequence as described herein above and further comprise at least one cysteine residue, such that the peptide monomers are covalently linked to one another via a disulfide bridge formed between a cysteine residue in one peptide monomer and a cysteine residue in another peptide monomer.

Typically, the cysteine is situated at the carboxy end of the peptide monomers.

Hereinthroughout, the phrases "disulfide bridge" and "disulfide bond" are used interchangeably, and describe a —S—S— bond.

The linker may comprise additional amino acids linked together by peptide bonds which serve as spacers such that the linker does not interfere with the biological activity of the final compound. The linker is preferably made up of amino acids linked together by peptide bonds. Thus, in preferred embodiments, the linker is made up of from 1 to 10 amino acids linked by peptide bonds, wherein the amino acids are selected from the 20 naturally occurring amino acids. Some of these amino acids may be glycosylated, as is well understood by those in the art. In a more preferred embodiment, besides cysteine the amino acids in the linker are selected from glycine, alanine, proline, asparagine, glutamine, and lysine. Even more preferably, besides cysteine, the linker is made up of a majority of amino acids that are sterically unhindered, such as glycine and alanine.

Thus, according to one embodiment the linker comprises the sequence cysteine-glycine.

Exemplary monomer sequences are thus set forth by the following sequences:

```
                              (SEQ ID NO: 8)
         CGHSIPTPILIFRSP, (SEQ ID NO: 9)
         CGHLLRPRRRKRPHSI, (SEQ ID NO: 10)
         CGRPRRRKRPHSIP, (SEQ ID NO: 11)
         CGSIPTPILIFRSP, (SEQ ID NO: 12)
         CGPHSIPTPILIFRSP
         or (SEQ ID NO: 13)
         CGHHLLRPRRRKR.
```

Non-peptide linkers are also possible. For example, alkyl linkers such as —NH—(CH$_2$)$_s$-C(O)—, wherein s=2-20 could be used. These alkyl linkers may further be substituted by any non-sterically hindering group such as lower alkyl (e.g., C$_1$-C$_6$) lower acyl, halogen (e.g., Cl, Br), CN, NH$_2$, phenyl, etc. An exemplary non-peptide linker is a PEG linker.

Thus, in some embodiments, at least one of monomers is PEGylated or chemically modified to another form. PEGylation of the molecules can be carried out, e.g., according to the methods described in Youngster et al., Curr Pharm Des (2002), 8:2139; Grace et al., J Interferon Cytokine Res (2001), 21: 1103; Pepinsky et al., J Pharmacol Exp Ther (2001), 297:1059; Pettit et al., J Biol Chem (1997), 272: 2312; Goodson et al. Biotechnology NY (1990), 8:343; Katre; J Immunol (1990), 144:209, Behrens et al US2006/ 0198819 A1, Klausen et al US2005/0113565 A1.

Any kind of polyethylene glycol is suitable for the present invention provided that the PEG-polypeptide-oligomer is still capable of antagonizing or neutralizing the binding of PLIF with its receptor which can be assayed according to methods known in the art.

Preferably, the polyethylene glycol of the polypeptide-dimer of the present invention is PEG 1000, 2000, 3000, 5000, 10000, 15000, 20000 or 40000 with PEG 20000 or 40000 being particularly preferred.

According to another embodiment the link is effected using a coupling agent.

The term "coupling agent", as used herein, refers to a reagent that can catalyze or form a bond between two or more functional groups intra-molecularly, inter-molecularly or both. Coupling agents are widely used to increase polymeric networks and promote crosslinking between polymeric chains, hence, in the context of some embodiments of the present invention, the coupling agent is such that can promote crosslinking between polymeric chains; or such that can promote crosslinking between amino functional groups and carboxylic functional groups, or between other chemically compatible functional groups of polymeric chains. In some embodiments of the present invention the term "coupling agent" may be replaced with the term "crosslinking agent". In some embodiments, one of the polymers serves as the coupling agent and acts as a crosslinking polymer.

By "chemically compatible" it is meant that two or more types of functional groups can react with one another so as to form a bond.

Exemplary functional groups which are typically present in gelatins and alginates include, but are not limited to, amines (mostly primary amines —$NH_2$), carboxyls (—$CO_2H$), sulfhydryls and hydroxyls (—SH and —OH respectively), and carbonyls (—COH aldehydes and —CO— ketones).

Primary amines occur at the N-terminus of polypeptide chains (called the alpha-amine), at the side chain of lysine (Lys, K) residues (the epsilon-amine), as found in gelatin, as well as in various naturally occurring polysaccharides and aminoglycosides. Because of its positive charge at physiologic conditions, primary amines are usually outward-facing (i.e., found on the outer surface) of proteins and other macromolecules; thus, they are usually accessible for conjugation.

Carboxyls occur at the C-terminus of polypeptide chain, at the side chains of aspartic acid (Asp, D) and glutamic acid (Glu, E), as well as in naturally occurring aminoglycosides and polysaccharides such as alginate. Like primary amines, carboxyls are usually on the surface of large polymeric compounds such as proteins and polysaccharides.

Sulfhydryls and hydroxyls occur in the side chain of cysteine (Cys, C) and serine, (Ser, S) respectively. Hydroxyls are abundant in polysaccharides and aminoglycosides.

Carbonyls as ketones or aldehydes can be form in glycoproteins, glycosides and polysaccharides by various oxidizing processes, synthetic and/or natural.

According to some embodiments of the present invention, the coupling agent can be selected according to the type of functional groups and the nature of the crosslinking bond that can be formed therebetween. For example, carboxyl coupling directly to an amine can be afforded using a carbodiimide type coupling agent, such as EDC; amines may be coupled to carboxyls, carbonyls and other reactive functional groups by N-hydroxysuccinimide esters (NHS-esters), imidoester, PFP-ester or hydroxymethyl phosphine; sulfhydryls may be coupled to carboxyls, carbonyls, amines and other reactive functional groups by maleimide, haloacetyl (bromo- or iodo-), pyridyldisulfide and vinyl sulfone; aldehydes as in oxidized carbohydrates, may be coupled to other reactive functional groups with hydrazide; and hydroxyl may be coupled to carboxyls, carbonyls, amines and other reactive functional groups with isocyanate.

Hence, suitable coupling agents that can be used in some embodiments of the present invention include, but are not limited to, carbodiimides, NHS-esters, imidoesters, PFP-esters or hydroxymethyl phosphines.

The peptides of the present invention can be biochemically synthesized such as by using standard solid phase techniques. These methods include exclusive solid phase synthesis, partial solid phase synthesis methods, fragment condensation, classical solution synthesis. Solid phase polypeptide synthesis procedures are well known in the art and further described by John Morrow Stewart and Janis Dillaha Young, Solid Phase Polypeptide Syntheses (2nd Ed., Pierce Chemical Company, 1984).

Synthetic peptides can be purified by preparative high performance liquid chromatography [Creighton T. (1983) Proteins, structures and molecular principles. WH Freeman and Co. N.Y.] and the composition of which can be confirmed via amino acid sequencing.

Recombinant techniques may also be used to generate the monomers of the present invention. To produce a peptide of the present invention using recombinant technology, a polynucleotide encoding the monomer of the present invention is ligated into a nucleic acid expression vector, which comprises the polynucleotide sequence under the transcriptional control of a cis-regulatory sequence (e.g., promoter sequence) suitable for directing constitutive, tissue specific or inducible transcription of the monomers of the present invention in the host cells.

In addition to being synthesizable in host cells, the monomers of the present invention can also be synthesized using in vitro expression systems. These methods are well known in the art and the components of the system are commercially available.

Typically, the monomers are synthesized as individual peptides, following which, depending on the linking moiety present in the monomers, linking is effected. For example, if the linking moiety is a cysteine residue, thiol oxidation is performed.

Thus, according to another aspect of the present invention there is provided a method of generating a dimeric peptide, the method comprising linking two isolated peptides, which each of the at least two isolated peptides comprise at least 6 consecutive amino acids and no more than 30 amino acids from the amino acid sequence as set forth in SEQ ID NO: 1.

When Cys residue is used as a linking moiety, disulfide bonds may be formed by oxidation thereof. In one embodiment the control of cysteine bond formation is exercised by choosing an oxidizing agent of the type and concentration effective to optimize formation of the multimer. Examples of oxidizing agent include iodine, dimethylsulfoxide (DMSO), potassium ferricyanide, and the like.

If the monomers comprise two or more cysteine residues, isomers resulting from disulfide bonds of different binding manner may be erroneously obtained. A peptide dimer wherein a disulfide bond is formed between intended cysteine residues can be prepared by selecting a particular combination of protecting groups for cysteine side chains. Examples of the combination of protecting groups include MeBzl (methylbenzyl) and Acm (acetamidemethyl) groups, Trt (trityl) and Acm groups, Npys (3-nitro-2-pyridylthio) and Acm groups, S-Bu-t (S-tert-butyl) and Acm groups, and the like. For example, in the case of a combination of MeBzl and Acm groups, the preparation can be carried out by a method comprising removing protecting groups other than MeBzl group and a protecting group(s) on the cysteine side chain, and subjecting the resulting monomer solution to air-oxidation to form a disulfide bond(s) between the deprotected cysteine residues, followed by deprotection and oxidization with iodine to form a disulfide bond(s) between the cysteine residues previously protected by Acm.

In embodiments where a peptide dimer is dimerized via a linker moiety, the linker may be incorporated into the peptide during peptide synthesis. For example, where a linker moiety contains two functional groups capable of serving as initiation sites for peptide synthesis and a third functional group (e.g., a carboxyl group or an amino group) that enables binding to another molecular moiety, the linker may be conjugated to a solid support. Thereafter, two peptide monomers may be synthesized directly onto the two reactive nitrogen groups of the linker moiety in a variation of the solid phase synthesis technique.

In alternate embodiments where a peptide dimer is dimerized by a linker moiety, the linker may be conjugated to the two peptide monomers of a peptide dimer after peptide synthesis. Such conjugation may be achieved by methods well established in the art. In one embodiment, the linker contains at least two functional groups suitable for attachment to the target functional groups of the synthesized peptide monomers. For example, a linker with two free amine groups may be reacted with the C-terminal carboxyl groups of each of two peptide monomers. In another example, linkers containing two carboxyl groups, either preactivated or in the presence of a suitable coupling reagent, may be reacted with the N-terminal or side chain amine groups, or C-terminal lysine amides, of each of two peptide monomers.

Monomers of the invention can be attached to water-soluble polymers (e.g., PEG) using any of a variety of chemistries to link the water-soluble polymer(s) to the receptor-binding portion of the molecule (e.g., peptide+spacer). A typical embodiment employs a single attachment junction for covalent attachment of the water soluble polymer(s) to the receptor-binding portion, however in alternative embodiments multiple attachment junctions may be used, including further variations wherein different species of water-soluble polymer are attached to the receptor-binding portion at distinct attachment junctions, which may include covalent attachment junction(s) to the spacer and/or to one or both peptide chains. In some embodiments, the dimer or higher order multimer will comprise distinct species of peptide chain (i.e., a heterodimer or other heteromultimer). By way of example and not limitation, a dimer may comprise a first peptide chain having a PEG attachment junction and the second peptide chain may either lack a PEG attachment junction or utilize a different linkage chemistry than the first peptide chain and in some variations the spacer may contain or lack a PEG attachment junction and the spacer, if PEGylated, may utilize a linkage chemistry different than that of the first and/or second peptide chains. An alternative embodiment employs a PEG attached to the spacer portion of the receptor-binding portion and a different water-soluble polymer (e.g., a carbohydrate) conjugated to a side chain of one of the amino acids of the peptide portion of the molecule.

The peptides of the present invention may also comprise non-amino acid moieties, such as for example, hydrophobic moieties (various linear, branched, cyclic, polycyclic or heterocyclic hydrocarbons and hydrocarbon derivatives) attached to the peptides; various protecting groups, especially where the compound is linear, which are attached to the compound's terminals to decrease degradation. Chemical (non-amino acid) groups present in the compound may be included in order to improve various physiological properties such; decreased degradation or clearance; decreased repulsion by various cellular pumps, improve immunogenic activities, improve various modes of administration (such as attachment of various sequences which allow penetration through various bathers, through the gut, etc.); increased specificity, increased affinity, decreased toxicity and the like.

According to one embodiment, the peptides of the present invention are attached to a sustained-release enhancing agent. Exemplary sustained-release enhancing agents include, but are not limited to hyaluronic acid (HA), alginic acid (AA), polyhydroxyethyl methacrylate (Poly-HEMA), polyethylene glycol (PEG), glyme and polyisopropylacrylamide.

Attaching the amino acid sequence component of the peptides of the invention to other non-amino acid agents may be by covalent linking, by non-covalent complexion, for example, by complexion to a hydrophobic polymer, which can be degraded or cleaved producing a compound capable of sustained release; by entrapping the amino acid part of the peptide in liposomes or micelles to produce the final peptide of the invention. The association may be by the entrapment of the amino acid sequence within the other component (liposome, micelle) or the impregnation of the amino acid sequence within a polymer to produce the final peptide of the invention.

Incubation Reaction

As mentioned, the method of this aspect of the present invention comprises incubating the white blood cell population (which comprises T cells and antigen presenting cells) with pathogenic cells in the presence of the multimeric peptide described above under conditions which allow activation and expansion of the T cells.

The phrase "activation of the T cells" refers to the induction of a cytotoxic activity in the T cells.

Preferably, the white blood cell population is incubated with the pathogenic cells and the multimeric peptide for at least one day, more preferably at least two days, three days, four days, five days, six days, seven days or more so as to ensure activation.

Additional agents may be included in the incubation including for example serum (e.g. fetal calf serum) or serum replacements. The peptide may be added throughout the incubation period or at one or two day intervals.

Preferably, the cells are cultured together with the peptide under conditions that ensure survival or propagation of the T cells. Such conditions include incubating at appropriate temperatures and pressure and in a medium that ensures cell survival. Exemplary media include RPMI or RPMI 1640 or AIM V.

The present invention contemplates expanding the T cells concomitantly with the activation and/or following the activation.

Expansion of T-cell cultures can be accomplished by any of a number of methods as are known in the arts. For example, T cells may be expanded utilizing non-specific T-cell receptor stimulation in the presence of feeder lymphocytes and either IL-2 or IL-15. The non-specific T-cell receptor stimulus can consist of around 30 ng/ml of OKT3, a mouse monoclonal anti-CD3 antibody available from Ortho, Raritan, N.J.

The T-cells may be modified to express a T-cell growth factor that promotes the growth and activation thereof. Any suitable methods of modification may be used. See, e.g., Sambrook and Russell, Molecular Cloning, 3$^{rd}$ ed., SCHL Press (2001). Desirably, modified T-cells express the T-cell growth factor at high levels. T-cell growth factor coding sequences, such as that of IL-2, are readily available in the art, as are promoters, the operable linkage of which to a T-cell growth factor coding sequence promote high-level expression.

Following generation of cytotoxic T cells, they may be isolated to generate a homogeneous population of isolated cytotoxic T cells.

Methods of isolating cytotoxic T cells from a mixed population of cells are known in the art and include for example isolating T cells based on the expression of a cell surface antigens such as CD8. This may be performed using flow cytometry. A multitude of flow cytometers are commercially available including for e.g. Becton Dickinson FACScan and FACScaliber (BD Biosciences, Mountain View, Calif.). Antibodies that may be used for FACS analysis are taught in Schlossman S, Boumell L, et al, [Leucocyte Typing V. New York: Oxford University Press; 1995] and are widely commercially available.

Additionally, or alternatively, a substrate including an antibody or a ligand capable of specifically binding cell surface markers present on "harmful" or non-relevant cells, can be used to effectively deplete these cells from the mixed population of cells.

The affinity substrate according to the present invention can be a column matrix such as, for example agarose, cellulose and the like, or beads such as, for example, magnetic beads onto which the antibodies described above, are immobilized.

Using the methods described above cytotoxic T cells and T cell lines may be obtained.

Thus, according to another aspect of the present invention there is provided a cytotoxic T cell line which comprises a multimeric peptide attached to an outer surface of T cells of the T cell line, the multimeric peptide comprising at least two peptide monomers linked to one another, each of the at least two peptide monomers comprising at least 6 consecutive amino acids from the amino acid sequence as set forth in SEQ ID NO: 1, wherein the at least two peptide monomers are each no longer than 30 amino acids, wherein the multimeric peptide is capable of reducing binding of PLIF to human leukocytes.

The present invention contemplates a T cell line wherein the multimeric peptide described herein above binds to at least 5% of the cells, at least 10% of the cells, at least 15% of the cells, at least 20% of the cells, at least 25% of the cells, at least 30% of the cells, at least 35% of the cells, at least 40% of the cells, at least 45% of the cells, at least 50% of the cells, at least 55% of the cells, at least 60% of the cells, at least 65% of the cells, at least 70% of the cells, at least 75% of the cells, at least 80% of the cells, at least 85% of the cells, at least 90% of the cells, at least 95% of the cells, at least 99% of the cells, or even to 100% of the cells.

Exemplary methods of assaying activities of T cell lines include $^{51}$CR release cytotoxicity assays (Cerundolo, V. et al. (1990) Nature 345:449-452) or lymphokine assays such as IFN-γ or TNF secretion assays [Schwartzentruber, D. et al., (1991) J. of Immunology 146:3674-3681].

The T cell lines described herein may be used for treating subjects having diseases which are amenable to treatment by adoptive immunotherapy (e.g. cancer, autoimmune diseases, HIV, hepatitis, HHV6, chronic fatigue syndrome).

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

As used herein, the phrase "subject in need thereof" refers to a subject which has the disease. The subject may be a mammal, e.g. a human. For example if the disease being treated is breast cancer, the subject is typically one being diagnosed with breast cancer, with or without metastasis, at any stage of the disease (e.g. IA, IB, IIA, IIB, IIC, IIIA, IIIB, IIIC or IV).

The T cell lines may be used immediately following generation or may be stored (e.g. frozen) and used when needed.

Exemplary cancers which may be treated using the T cell lines described herein include, but are not limited to, adrenocortical carcinoma, hereditary; bladder cancer; breast cancer; breast cancer, ductal; breast cancer, invasive intraductal; breast cancer, sporadic; breast cancer, susceptibility to; breast cancer, type 4; breast cancer, type 4; breast cancer-1; breast cancer-3; breast-ovarian cancer; Burkitt's lymphoma; cervical carcinoma; colorectal adenoma; colorectal cancer; colorectal cancer, hereditary nonpolyposis, type 1; colorectal cancer, hereditary nonpolyposis, type 2; colorectal cancer, hereditary nonpolyposis, type 3; colorectal cancer, hereditary nonpolyposis, type 6; colorectal cancer, hereditary nonpolyposis, type 7; dermatofibrosarcoma protuberans; endometrial carcinoma; esophageal cancer; gastric cancer, fibrosarcoma, glioblastoma multiforme; glomus tumors, multiple; hepatoblastoma; hepatocellular cancer; hepatocellular carcinoma; leukemia, acute lymphoblastic; leukemia, acute myeloid; leukemia, acute myeloid, with eosinophilia; leukemia, acute nonlymphocytic; leukemia, chronic myeloid; Li-Fraumeni syndrome; liposarcoma, lung cancer; lung cancer, small cell; lymphoma, non-Hodgkin's; lynch cancer family syndrome II; male germ cell tumor; mast cell leukemia; medullary thyroid; medulloblastoma; melanoma, meningioma; multiple endocrine neoplasia; myeloid malignancy, predisposition to; myxosarcoma, neuroblastoma; osteosarcoma; ovarian cancer; ovarian cancer, serous; ovarian carcinoma; ovarian sex cord tumors; pancreatic cancer; pancreatic endocrine tumors; paraganglioma, familial nonchromaffin; pilomatricoma; pituitary tumor, invasive; prostate adenocarcinoma; prostate cancer; renal cell carcinoma, papillary, familial and sporadic; retinoblastoma; rhabdoid predisposition syndrome, familial; rhabdoid tumors; rhabdomyosarcoma; small-cell cancer of lung; soft tissue sarcoma, squamous cell carcinoma, head and neck; T-cell acute lymphoblastic leukemia; Turcot syndrome with glioblastoma; tylosis with esophageal cancer; uterine cervix carcinoma, Wilms' tumor, type 2; and Wilms' tumor, type 1, etc.

Preferably, the cancer is breast cancer, melanoma, lung carcinoma, colon cancer, prostate cancer, ovarian carcinoma, renal cell carcinoma, glioma, Hodgkin's lymphoma, non-Hodgkin's lymphoma, acute lymphatic leukemia (ALL) and the like. The cancer may be metastatic or non-metastatic.

According to a particular embodiment, the cancer is breast cancer (e.g. triple negative breast cancer).

It will be appreciated that preparation of cytotoxic T cell lines for treatment of a disease in a particular subject may be effected using components which are autologous to that subject. Thus, for example, the present invention contemplates using T cells retrieved from the patient for generating the T cell line. Additionally and/or alternatively the pathogenic cells used to stimulate the T cells may be autologous to the subject.

The present inventors have shown that as long as the pathogenic cells used to activate the T cells share at least one HLA class I allele with the pathogenic cells present in the subject the generated T cell lines will be cytotoxic and effective at treating the disease in the subject.

Thus, the pathogenic cells used to stimulate the T cells are preferably allogeneic with the pathogenic cells in the subject. Verdegaal et al., Human Immunology 60, 1196-1206, 1999, the contents of which are incorporated by reference herein teaches various tumors which share HLA class I alleles.

Thus, the present invention contemplates activating T cells with breast cancer cells and using the activated T cells for treating renal cell carcinoma, colon cancer, renal cancer and/or melanoma.

In addition, the present invention contemplates activating T cells with one type of breast cancer cells and using the activated T cells for treating another type of breast cancer (as long as the cancers share HLA class I alleles). For example, the present inventors have shown that activating T cells with the MCF7 breast cancer cell line generates T cells lines which are cytotoxic against MDA-MB231 cells (a breast cancer triple negative cell line.

The T cell lines may be provided per se or as part of a pharmaceutical composition.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the T cells accountable for the biological effect.

Hereinafter, the phrases "physiologically acceptable carrier" and "pharmaceutically acceptable carrier" which may be interchangeably used refer to a carrier or a diluent that does not abrogate the biological activity and properties of the administered compound. The carrier may also include biological or chemical substances that modulate the immune response.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

The T-cells can be administered by any suitable route as known in the art. For example, the T-cells may be administered as an intra-arterial or intravenous infusion, which preferably lasts approximately 30-60 minutes. Other examples of routes of administration include intraperitoneal, intrathecal and intralymphatic.

A suitable dose of T-cells to be administered is from about $2.3 \times 10^{10}$ T-cells to about $13.7 \times 10^{10}$ T-cells.

According to one embodiment, the T cells are administered to the subject together with the C24D peptide.

Additionally, or alternatively, the T cells are administered to the subject with a T-cell growth factor. The T-cell growth factor can be any suitable growth factor that promotes the growth and activation of the T-cells administered. Examples of suitable T-cell growth factors include IL-2, IL-7 and IL-15, which can be used alone or in various combinations, such as IL-2 and IL-7, IL-2 and IL-15, IL-7 and IL-15, or IL-2, IL-7 and IL-15. IL-2 is available from Chiron, Emerwlle, Calif., whereas IL-7 is available from Cytheris, Vanves, Frances. IL-15 can be obtained from PeproTech, Inc., Rocky Hill, N.J.

The T-cell growth factor can be administered by any suitable route. If more than one T-cell growth factor is administered, they can be administered simultaneously or sequentially, in any order, and by the same route or different routes. According to one embodiment, the T-cell growth factor, such as IL-2, is administered intravenously as a bolus injection. A typical dosage of IL-2 is about 720,000 IU/kg, administered three times daily until tolerance.

The T cell lines may be administered in conjunction with nonmyeloablative lymphodepleting chemotherapy. The nonmyeloablative lymphodepleting chemotherapy can comprise the administration of cyclophosphamide and fludarabine, particularly if the cancer is melanoma. A preferred route of administering cyclophosphamide and fludarabine is intravenously. Likewise, any suitable dose of cyclophosphamide and fludarabine can be administered.

The T cell lines described herein may be stored individually or may be comprised in a bank, each cell line being categorized according to a particular parameter (e.g. according to the HLA type of the pathogenic cell used for activation).

Thus, according to still another aspect of the present invention there is provided a method of producing a T cell line bank comprising: generating the T cell lines described herein from a plurality of subjects to obtain a plurality of separate T cell lines and storing the T cell lines.

The T cell line bank of this aspect of the present invention is a physical collection of one or more T cell lines derived from patients with a particular disorder (e.g. cancer). Such banks preferably contain more than one sample (i.e., aliquot) of each T cell line. The bank may also contain one or more samples of the feeder cells, expansion agent and/or serum used to expand the MSC populations.

The T cell lines are stored under appropriate conditions (typically by freezing) to keep them alive and functioning. According to one embodiment, the T cell lines are stored as cryopreserved populations. Other preservation methods are described in U.S. Pat. Nos. 5,656,498, 5,004,681, 5,192,553, 5,955,257, and 6,461,645.

As used herein the term "about" refers to ±10%.

The terms "comprises", "comprising", "includes", "including", "having" and their conjugates mean "including but not limited to".

The term "consisting of" means "including and limited to".

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Generation of Specific Cytotoxic T Cell Lines Against Breast Cancer Cells MCF-7 and T47D Materials and Methods Breast Cancer Cell Cultures The MCF-7 and T47D human breast cancer cell lines were maintained in monolayer cultures in RPMI-1640 medium supplemented with 10% fetal calf serum. For passages, confluent monolayer cultures were trypsinized with trypsin/EDTA solution (0.25% and 0.05%, respectively), washed once, and seeded in culture medium.

Preparation of PBMC

Buffy coats from blood bank donors were layered onto Lymphoprep solution (Nycomed, Oslo, Norway) and spun at 2000 rpm for 20 minutes. The interface layer was collected, washed twice, counted, and resuspended in PBS; pH 7.4 to the desired cell concentration.

Breast Cancer Cells and PBMC Co-Culture In Vitro, for Primary Activation

MCF-7 and T47D were maintained in RPMI+fetal calf serum (10%). One day prior to the start of the experiment, the medium was replaced with RPMI+human AB serum (10%). PBMC ($1 \times 10^6$) were added to MCF-7 or T47D ($0.1 \times 10^6$) at Effector/Target (E/T) 10:1 ratio, in a final volume of 1 ml dispensed into 24-well microtiter plates. The cells were treated with C24D (30 µg/ml) at 0, 24 and 48 hours. The cell cultures without treatment were used for comparison. Culture Plates were subjected to microscopic evaluation on experimental days 5 and 7.

Development of a Specific Anti-Breast Cancer Cytotoxic Cell Lines (CTL)

Figure 1:
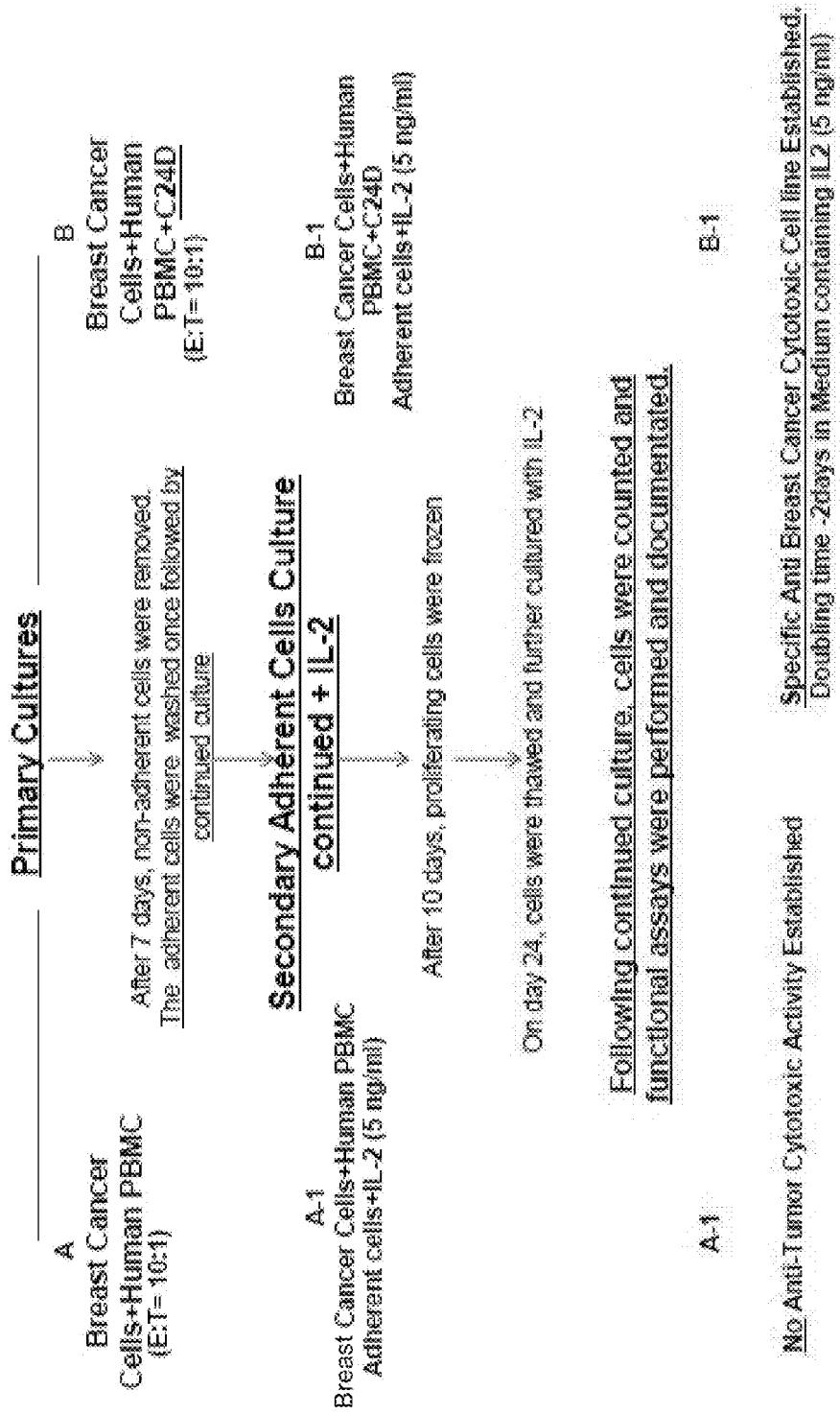

After tumor cell cytolysis was observed in the primary culture (days 5-7), the nonadherent cells (tumor and PBMC) were removed from the wells, and fresh medium containing human IL-2 (5 ng/ml) was added to the wells containing the remaining adherent cells. The cultures were treated 3 times a week with RPMI-1640 containing 10% human AB serum and IL-2 (5 ng/ml). The outline for generation of specific cytotoxic T cell lines is presented in FIG. 1.

Tumor Cell Cytotoxicity and Apoptosis Assays

MTT Viability Test:

MTT reduction, which is an indicator of cellular metabolic activity, was measured, as previously described (Berridge et al., Biochemica 1996; 4:15-20). In brief, breast cancer cells were incubated for 4 h with lymphocytes at different E:T ratios. At 2 h incubation, 50 µl of 0.25% (w/v) solution of MTT in PBS buffer (NaCl 136.9 mM, KCl 2.68 mM, Na2HPO4 8.1 mM, KH2PO4 1.47 mM, pH 7.4) was added to the media and further incubated for 2 h. At the end of this incubation, the nonadherent cells were removed and the remaining adherent tumor cells were washed twice with PBS, and dissolved in a mixture of dimethyl-sulfoxide (Sigma-Aldrich), 5% (w/v) sodium dodecyl sulfate (SDS) and 1% (v/v) 1N hydrochloric acid. After an additional brief agitation on a microtiter plate shaker, we measured the absorption at 570/650 nm with a plate reader (FluoStar, BMG Labtechnology, Offenburg, Germany).

Data Analysis:

The viability was calculated with regard to the untreated breast cancer cells only, control [y0], which was set to 100% viability. A lysis control [y100], wherein the cells were treated with 0.5% triton X-100, was set to 0% viability. This was found to be sufficient to induce 100% cell death. Mean values from 8 wells were determined.

Annexin V Test for Apoptosis:

The ability of the specific anti-T47D CTL to induce apoptotic cell death in T47D breast cancer cells was evaluated using Annexin V apoptosis, as previously described (Vermes et al., J Immunol Methods 1995; 184:39-51). In brief, $5 \times 10^5$ tumor cells were plated in a 24-well microtiter plate. This was followed by the addition of $1.7 \times 10^5$ CTL (E:T ratio 1:3) in 0.4 RPMI medium containing 10% human AB serum. The plate was centrifuged at 1300 rpm for 4 min, and the mixtures were either immediately cooled on ice (5 min sample) or further cultured for 2 hours at 37° C. The cells were collected and further reacted with FITC Annexin and propidium iodide (PI) V/PI Detection Kit-FITC (eBioscience), according to the manufacturer's instructions.

Light-scatter characteristics were used to distinguish the tumor cells from the lymphocytes, such that only the tumor cells were counted in the analysis and the percentage of FITC-conjugated Annexin V-positive cells was analyzed by flow cytometry (Becton Dickinson).

Results

Primary Activation of Anti-MCF-7 and T47D Breast Cancer T Cells by C24D Treatment In Vitro T47D and MCF-7 tumor cells grew as a monolayer in tissue culture plates, as demonstrated by microscopic examination (FIGS. 2A, 3A, 4A, 5A). The addition of PBMC to tumor cells at E:T ratio of 10:1, did not affect their growth at days 5 and 7 of the culture (FIGS. 2B, 3B, 4B, 5B). In contrast, C24D treatment of MCF-7 and T47D cells, cultured with PBMC for 5-7 days at 37° C., resulted in lysis of the cancer cells as seen in microscopic examination (FIGS. 2C, 3C, 4C, 5C) and by a cytotoxic assay which showed cytolysis of 25-33% of T47D and MCF7 tumor cells respectively, (FIG. 6).

Following tumor cells cytolysis, immune cells remained adherent on the culture plates (FIGS. 2C, 3C, 4C, 5C). Neither cytolysis nor presence of immune adherent cells was observed in the untreated control cultures of tumor cells and PBMC (FIGS. 2B, 3B, 4B, 5B). The adherent cells were identified by FACS analysis as $CD3^+$ T cells and $CD14^+$ macrophages.

In Vitro Generation of Breast Cancer Cytotoxic T Cell Lines (CTL)

The adherent $CD3^+$ T cells observed following tumor cells cytolysis started to proliferate following IL-2 addition to the 7 day primary C24D-treated tumor-lymphocyte cultures. It is noteworthy that residual tumor cells which remained in the culture underwent complete cytolysis following IL-2 addition and further T cell proliferation in the culture. The T cells multiplied exponentially in continued culture medium containing IL-2 without further C24D treatment, (doubling time 48 hours). The cytotoxic T cell lines were frozen and stored in liquid nitrogen for further use. In untreated tumor-PBMC cultures (control), no cytotoxic T cell lines were developed.

Anti-T47D Tumor Cell Cytotoxicity

The extent of immunity elicited by the induced anti-T47D CTL was analyzed by microscopic examination (FIG. 7B). It was also measured by the MTT quantitative cytotoxic assay. After 4 hours incubation of anti-T47D CTL with cancer cells at an E:T ratio 1:5, 60% of T47D cells were lysed. The cytotoxic activity of the CTL was increased in comparison to that of the primary activation cultures induced at E:T ratio of 10:1, resulting in 25% T47D tumor cell cytotoxicity after 7 days in culture.

It was further revealed by microscopic examination and cytotoxic tests that the anti-T47D CTL was tumor specific and was not cytotoxic to MCF7 cells (FIGS. 7D, 8).

Induction of Apoptosis of T47D Tumor Cells In Vitro

In the early stages of apoptosis, changes occur at the cell surface. One of the plasma membrane alterations is the translocation of phosphatidylserine (PS) from the inner side of the plasma membrane to the cell.

Annexin V is a Ca+ dependent phospholipid-binding protein with high affinity for PS. Hence, this protein can be used as a sensitive probe for PS exposure on the cell membrane.

T47D cytotoxic cell line induced early apoptosis of T47D tumor cells, as evidenced by the appearance of 26.2% Annexin V positive tumor cells after 2 hours of incubation at E:T ratio of 1:3, as compared to 3.4% at 0 h (FIGS. 9A-B, 10).

Example 2

Broadly Reactive Cytotoxic T Cell Lines (CTL) for HLA Class I Restricted Breast Cancer Materials and Methods Breast Cancer Cell Cultures The MCF7, T47D and MDA-MB231 human breast carcinoma cell lines were maintained in monolayer cultures in RPMI-1640 medium supplemented with 10% fetal calf serum. For passages, confluent monolayer cultures were trypsinized with trypsin/EDTA solution (0.25%/0.05%, respectively), washed once, and seeded in culture medium.

Anti-MCF7 and anti-T47D CTL were maintained in cultures treated 3 times a week with RPMI-1640 containing 10% human AB serum and IL2 (5 ng/ml).

Cytokine Production Evaluation

Breast cancer cells (MCF7, T47D and MDA-MB231) were incubated for 5-20 hours with CTL at different E/T ratios. At the end of the incubation, supernatants were collected and cytokine levels were measured in ELISA.

The ELISA kits for the human cytokines TNF-α and IFN-γ were purchased from DPC, and R&D Systems, USA. These kits were used to quantify the indicated cytokines production in the supernatants, according to the manufacturer's instructions.

MTT Viability Test

Breast cancer cells (MCF7, T47D and MDA-MB231) were incubated for 5 hours with CTL at different E/T ratios. Initially, fresh medium was applied to the treated cells. After 5 hours, 50 µl of a 0.25% (w/v) solution of MTT in phosphate buffered saline (PBS) buffer (NaCl 136.9 mM, KCl 2.68 mM, Na2HPO8.1 mM, KH2PO4 1.47 mM, pH 7.4) was added to the media. Two hours later, the nonadherent cells were removed and the remaining adherent tumor cells were washed twice with PBS, and dissolved in a mixture of dimethyl-sulfoxide (Sigma-Aldrich), 5% (w/v) sodium dodecyl sulphate (SDS) and 1% (v/v) 1N hydrochloric acid. After an additional brief agitation on a microtiter plate shaker, the absorption at 570/650 nm was measured with a plate reader (FluoStar, BMG Labtechnology, Offenburg, Germany).

Data Analysis

The viability was calculated with regard to the untreated breast cancer cell only, control [y0], which was set to 100% viability. A lysis control [y100], where the cells were treated with 0.5% triton X-100 was set to 0% viability, which was found to be sufficient to induce 100% cell death. Mean values from eight wells were determined.

Results

MDA-MB231 Cytotoxicity by Anti-MCF7 CTL

The extent of MDA-MB231 cytotoxicity by anti-MCF7 CTL following re-stimulation, was analyzed by microscopic examination (FIGS. 11A-D).

Cytotoxicity of MDA-MB231 cells was observed only when treated with the HLA-A2$^+$ identical anti-MCF7 CTL (FIG. 11A), but not with anti-HLA-A2$^-$ T47D CTL (FIG. 11B). Control non-CTL PBMC were not cytolytic to MDA-MB231 cells (FIGS. 11C,D).

Cytotoxicity was also measured quantitatively by the MTT assay. As seen in FIG. 12, incubation of anti-MCF-7 CTL with both MCF7 and MDA-MB231 target cells at E:T ratio 1:1 for 5 hours resulted in 70% and 80% cytotoxicity, respectively, whereas anti-T47D CTL activity was restricted to T47D cells. These results demonstrate that anti-MCF-7 CTL is broadly reactive, tumor specific and HLA-A2$^+$ class I restricted CTL.

MDA-MB231 Restimulates MCF7 CTL to Secrete Interferon-γ

The magnitude of antigenic re-stimulation of different CTL was measured by the level of interferon-γ secreted by anti-MCF7 and anti-T47D CTL following incubation with their respective tumor target cells, as well as with MDA-MB231. As seen in FIG. 13, re-stimulation of anti-MCF7 and anti-T47D CTL with their respective target cells resulted in increased Interferon-γ secretion. In addition, high levels of interferon γ were measured following cross stimulation of anti-MCF-7 CTL with MDA-MB231. The amount of interferon secreted was proportional to the ratio of CTL effector to tumor target (FIG. 14).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An in-vitro method of activating T cells, the method comprising incubating tumor-specific T cells with allogeneic HLA-A2 matched tumor cells in the presence of a dimer comprising two identical peptide monomers covalently linked to one another, each of said two peptide monomers comprising the amino acid sequence as set forth in SEQ ID NO: 1, wherein said two peptide monomers are each no longer than 30 amino acids, wherein said method is carried out under conditions which allow expansion of said tumor-specific T cells.

2. An in vitro method of increasing the cytotoxicity of tumor-specific T cells comprising incubating allogeneic HLA-A2 matched tumor cells with tumor-specific T cells in the presence of a dimer comprising two identical peptide monomers covalently linked to one another, each of said two peptide monomers comprising the amino acid sequence as set forth in SEQ ID NO: 1, wherein said two peptide monomers are each no longer than 30 amino acids, wherein the method is carried out under conditions which allow for the generation of activated tumor-specific T cells that are cytotoxic to said tumor cells, thereby increasing the cytotoxicity of the T cells.

3. The method of claim 2, further comprising expanding said activated T cells.

4. The method of claim 3, wherein said expanding is effected using interleukin 2 (IL-2).

5. The method of claim 1, wherein said cancer cells comprise breast cancer cells.

6. The method of claim 1, wherein said T cells are comprised in peripheral mononuclear blood cells (PBMCs).

7. The method of claim 1, wherein the peptide is capable of increasing INF-γ secretion from activated leukocytes.

8. The method of claim 1, wherein each of said two peptide monomers is attached to a Cysteine (Cys) residue.

9. The method of claim 1, wherein the dimer is capable of reducing binding of PLIF to human leukocytes.

* * * * *

SEQUENCE LISTING

```
<160> NUMBER OF SEQ ID NOS: 100

<210> SEQ ID NO 1
<211> LENGTH: 25
<212> TYPE: PRT
<213> ORGANISM: Artificial sequence
<220> FEATURE:
<223> OTHER INFORMATION: Placental Immunoregulatory Ferritin (PLIF)
      derived polypeptide sequence

<400> SEQUENCE: 1

His His Leu Leu Arg Pro Arg Arg Arg Lys Arg Pro His Ser Ile Pro
1               5                   10                  15

Thr Pro Ile Leu Ile Phe Arg Ser Pro
            20                  25

<210> SEQ ID NO 2
<211> LENGTH: 13
<212> TYPE: PRT
<213> ORGANISM: Artificial sequence
<220> FEATURE:
<223> OTHER INFORMATION: A monomer of the multimeric peptide

<400> SEQUENCE: 2

His Ser Ile Pro Thr Pro Ile Leu Ile Phe Arg Ser Pro
1               5                   10

<210> SEQ ID NO 3
<211> LENGTH: 14
<212> TYPE: PRT
<213> ORGANISM: Artificial sequence
<220> FEATURE:
<223> OTHER INFORMATION: A monomer of the multimeric peptide
```

<400> SEQUENCE: 3

His Leu Leu Arg Pro Arg Arg Arg Lys Arg Pro His Ser Ile
1               5                   10

<210> SEQ ID NO 4
<211> LENGTH: 12
<212> TYPE: PRT
<213> ORGANISM: Artificial sequence
<220> FEATURE:
<223> OTHER INFORMATION: A monomer of the multimeric peptide

<400> SEQUENCE: 4

Arg Pro Arg Arg Arg Lys Arg Pro His Ser Ile Pro
1               5                   10

<210> SEQ ID NO 5
<211> LENGTH: 12
<212> TYPE: PRT
<213> ORGANISM: Artificial sequence
<220> FEATURE:
<223> OTHER INFORMATION: A monomer of the multimeric peptide

<400> SEQUENCE: 5

Ser Ile Pro Thr Pro Ile Leu Ile Phe Arg Ser Pro
1               5                   10

<210> SEQ ID NO 6
<211> LENGTH: 14
<212> TYPE: PRT
<213> ORGANISM: Artificial sequence
<220> FEATURE:
<223> OTHER INFORMATION: A monomer of the multimeric peptide

<400> SEQUENCE: 6

Pro His Ser Ile Pro Thr Pro Ile Leu Ile Phe Arg Ser Pro
1               5                   10

<210> SEQ ID NO 7
<211> LENGTH: 11
<212> TYPE: PRT
<213> ORGANISM: Artificial sequence
<220> FEATURE:
<223> OTHER INFORMATION: A monomer of the multimeric peptide

<400> SEQUENCE: 7

His His Leu Leu Arg Pro Arg Arg Arg Lys Arg
1               5                   10

<210> SEQ ID NO 8
<211> LENGTH: 15
<212> TYPE: PRT
<213> ORGANISM: Artificial sequence
<220> FEATURE:
<223> OTHER INFORMATION: Exemplary monomer of the multimeric peptide

<400> SEQUENCE: 8

Cys Gly His Ser Ile Pro Thr Pro Ile Leu Ile Phe Arg Ser Pro
1               5                   10                  15

<210> SEQ ID NO 9
<211> LENGTH: 16
<212> TYPE: PRT
<213> ORGANISM: Artificial sequence
<220> FEATURE:
<223> OTHER INFORMATION: Exemplary monomer of the multimeric peptide

```
<400> SEQUENCE: 9

Cys Gly His Leu Leu Arg Pro Arg Arg Arg Lys Arg Pro His Ser Ile
1               5                   10                  15

<210> SEQ ID NO 10
<211> LENGTH: 14
<212> TYPE: PRT
<213> ORGANISM: Artificial sequence
<220> FEATURE:
<223> OTHER INFORMATION: Exemplary monomer of the multimeric peptide

<400> SEQUENCE: 10

Cys Gly Arg Pro Arg Arg Arg Lys Arg Pro His Ser Ile Pro
1               5                   10

<210> SEQ ID NO 11
<211> LENGTH: 14
<212> TYPE: PRT
<213> ORGANISM: Artificial sequence
<220> FEATURE:
<223> OTHER INFORMATION: Exemplary monomer of the multimeric peptide

<400> SEQUENCE: 11

Cys Gly Ser Ile Pro Thr Pro Ile Leu Ile Phe Arg Ser Pro
1               5                   10

<210> SEQ ID NO 12
<211> LENGTH: 16
<212> TYPE: PRT
<213> ORGANISM: Artificial sequence
<220> FEATURE:
<223> OTHER INFORMATION: Exemplary monomer of the multimeric peptide

<400> SEQUENCE: 12

Cys Gly Pro His Ser Ile Pro Thr Pro Ile Leu Ile Phe Arg Ser Pro
1               5                   10                  15

<210> SEQ ID NO 13
<211> LENGTH: 13
<212> TYPE: PRT
<213> ORGANISM: Artificial sequence
<220> FEATURE:
<223> OTHER INFORMATION: Exemplary monomer of the multimeric peptide

<400> SEQUENCE: 13

Cys Gly His His Leu Leu Arg Pro Arg Arg Arg Lys Arg
1               5                   10

<210> SEQ ID NO 14
<211> LENGTH: 15
<212> TYPE: PRT
<213> ORGANISM: Artificial sequence
<220> FEATURE:
<223> OTHER INFORMATION: Placental Immunoregulatory Ferritin (PLIF)
      derived polypeptide sequence

<400> SEQUENCE: 14

Arg Pro His Ser Ile Pro Thr Pro Ile Leu Ile Phe Arg Ser Pro
1               5                   10                  15

<210> SEQ ID NO 15
<211> LENGTH: 6
<212> TYPE: PRT
<213> ORGANISM: Artificial sequence
<220> FEATURE:
<223> OTHER INFORMATION: Exemplary monomer of the multimeric peptide
```

```
<400> SEQUENCE: 15

His His Leu Leu Arg Pro
1               5

<210> SEQ ID NO 16
<211> LENGTH: 6
<212> TYPE: PRT
<213> ORGANISM: Artificial sequence
<220> FEATURE:
<223> OTHER INFORMATION: Exemplary monomer of the multimeric peptide

<400> SEQUENCE: 16

His Leu Leu Arg Pro Arg
1               5

<210> SEQ ID NO 17
<211> LENGTH: 6
<212> TYPE: PRT
<213> ORGANISM: Artificial sequence
<220> FEATURE:
<223> OTHER INFORMATION: Exemplary monomer of the multimeric peptide

<400> SEQUENCE: 17

Leu Leu Arg Pro Arg Arg
1               5

<210> SEQ ID NO 18
<211> LENGTH: 6
<212> TYPE: PRT
<213> ORGANISM: Artificial sequence
<220> FEATURE:
<223> OTHER INFORMATION: Exemplary monomer of the multimeric peptide

<400> SEQUENCE: 18

Leu Arg Pro Arg Arg Lys
1               5

<210> SEQ ID NO 19
<211> LENGTH: 6
<212> TYPE: PRT
<213> ORGANISM: Artificial sequence
<220> FEATURE:
<223> OTHER INFORMATION: Exemplary monomer of the multimeric peptide

<400> SEQUENCE: 19

Arg Pro Arg Arg Lys Arg
1               5

<210> SEQ ID NO 20
<211> LENGTH: 6
<212> TYPE: PRT
<213> ORGANISM: Artificial sequence
<220> FEATURE:
<223> OTHER INFORMATION: Exemplary monomer of the multimeric peptide

<400> SEQUENCE: 20

Pro Arg Arg Lys Arg Pro
1               5

<210> SEQ ID NO 21
<211> LENGTH: 6
<212> TYPE: PRT
<213> ORGANISM: Artificial sequence
<220> FEATURE:
<223> OTHER INFORMATION: Exemplary monomer of the multimeric peptide

<400> SEQUENCE: 21
```

Arg Arg Lys Arg Pro His
1               5

<210> SEQ ID NO 22
<211> LENGTH: 6
<212> TYPE: PRT
<213> ORGANISM: Artificial sequence
<220> FEATURE:
<223> OTHER INFORMATION: Exemplary monomer of the multimeric peptide

<400> SEQUENCE: 22

Arg Lys Arg Pro His Ser
1               5

<210> SEQ ID NO 23
<211> LENGTH: 6
<212> TYPE: PRT
<213> ORGANISM: Artificial sequence
<220> FEATURE:
<223> OTHER INFORMATION: Exemplary monomer of the multimeric peptide

<400> SEQUENCE: 23

Lys Arg Pro His Ser Ile
1               5

<210> SEQ ID NO 24
<211> LENGTH: 6
<212> TYPE: PRT
<213> ORGANISM: Artificial sequence
<220> FEATURE:
<223> OTHER INFORMATION: Exemplary monomer of the multimeric peptide

<400> SEQUENCE: 24

Arg Pro His Ser Ile Pro
1               5

<210> SEQ ID NO 25
<211> LENGTH: 6
<212> TYPE: PRT
<213> ORGANISM: Artificial sequence
<220> FEATURE:
<223> OTHER INFORMATION: Exemplary monomer of the multimeric peptide

<400> SEQUENCE: 25

Pro His Ser Ile Pro Thr
1               5

<210> SEQ ID NO 26
<211> LENGTH: 6
<212> TYPE: PRT
<213> ORGANISM: Artificial sequence
<220> FEATURE:
<223> OTHER INFORMATION: Exemplary monomer of the multimeric peptide

<400> SEQUENCE: 26

His Ser Ile Pro Thr Pro
1               5

<210> SEQ ID NO 27
<211> LENGTH: 6
<212> TYPE: PRT
<213> ORGANISM: Artificial sequence
<220> FEATURE:
<223> OTHER INFORMATION: Exemplary monomer of the multimeric peptide

<400> SEQUENCE: 27

Ser Ile Pro Thr Pro Ile
1               5

<210> SEQ ID NO 28
<211> LENGTH: 6
<212> TYPE: PRT
<213> ORGANISM: Artificial sequence
<220> FEATURE:
<223> OTHER INFORMATION: Exemplary monomer of the multimeric peptide

<400> SEQUENCE: 28

Ile Pro Thr Pro Ile Leu
1               5

<210> SEQ ID NO 29
<211> LENGTH: 6
<212> TYPE: PRT
<213> ORGANISM: Artificial sequence
<220> FEATURE:
<223> OTHER INFORMATION: Exemplary monomer of the multimeric peptide

<400> SEQUENCE: 29

Pro Thr Pro Ile Leu Ile
1               5

<210> SEQ ID NO 30
<211> LENGTH: 6
<212> TYPE: PRT
<213> ORGANISM: Artificial sequence
<220> FEATURE:
<223> OTHER INFORMATION: Exemplary monomer of the multimeric peptide

<400> SEQUENCE: 30

Thr Pro Ile Leu Ile Phe
1               5

<210> SEQ ID NO 31
<211> LENGTH: 6
<212> TYPE: PRT
<213> ORGANISM: Artificial sequence
<220> FEATURE:
<223> OTHER INFORMATION: Exemplary monomer of the multimeric peptide

<400> SEQUENCE: 31

Pro Ile Leu Ile Phe Arg
1               5

<210> SEQ ID NO 32
<211> LENGTH: 6
<212> TYPE: PRT
<213> ORGANISM: Artificial sequence
<220> FEATURE:
<223> OTHER INFORMATION: Exemplary monomer of the multimeric peptide

<400> SEQUENCE: 32

Ile Leu Ile Phe Arg Ser
1               5

<210> SEQ ID NO 33
<211> LENGTH: 6
<212> TYPE: PRT
<213> ORGANISM: Artificial sequence
<220> FEATURE:
<223> OTHER INFORMATION: Exemplary monomer of the multimeric peptide

<400> SEQUENCE: 33

Leu Ile Phe Arg Ser Pro

<210> SEQ ID NO 34
<211> LENGTH: 7
<212> TYPE: PRT
<213> ORGANISM: Artificial sequence
<220> FEATURE:
<223> OTHER INFORMATION: Exemplary monomer of the multimeric peptide

<400> SEQUENCE: 34

His His Leu Leu Arg Pro Arg
1               5

<210> SEQ ID NO 35
<211> LENGTH: 7
<212> TYPE: PRT
<213> ORGANISM: Artificial sequence
<220> FEATURE:
<223> OTHER INFORMATION: Exemplary monomer of the multimeric peptide

<400> SEQUENCE: 35

His Leu Leu Arg Pro Arg Arg
1               5

<210> SEQ ID NO 36
<211> LENGTH: 7
<212> TYPE: PRT
<213> ORGANISM: Artificial sequence
<220> FEATURE:
<223> OTHER INFORMATION: Exemplary monomer of the multimeric peptide

<400> SEQUENCE: 36

Leu Leu Arg Pro Arg Arg Lys
1               5

<210> SEQ ID NO 37
<211> LENGTH: 7
<212> TYPE: PRT
<213> ORGANISM: Artificial sequence
<220> FEATURE:
<223> OTHER INFORMATION: Exemplary monomer of the multimeric peptide

<400> SEQUENCE: 37

Leu Arg Pro Arg Arg Lys Arg
1               5

<210> SEQ ID NO 38
<211> LENGTH: 7
<212> TYPE: PRT
<213> ORGANISM: Artificial sequence
<220> FEATURE:
<223> OTHER INFORMATION: Exemplary monomer of the multimeric peptide

<400> SEQUENCE: 38

Arg Pro Arg Arg Lys Arg Pro
1               5

<210> SEQ ID NO 39
<211> LENGTH: 7
<212> TYPE: PRT
<213> ORGANISM: Artificial sequence
<220> FEATURE:
<223> OTHER INFORMATION: Exemplary monomer of the multimeric peptide

<400> SEQUENCE: 39

Pro Arg Arg Lys Arg Pro His
1               5

<210> SEQ ID NO 40
<211> LENGTH: 7
<212> TYPE: PRT
<213> ORGANISM: Artificial sequence
<220> FEATURE:
<223> OTHER INFORMATION: Exemplary monomer of the multimeric peptide

<400> SEQUENCE: 40

Arg Arg Lys Arg Pro His Ser
1               5

<210> SEQ ID NO 41
<211> LENGTH: 7
<212> TYPE: PRT
<213> ORGANISM: Artificial sequence
<220> FEATURE:
<223> OTHER INFORMATION: Exemplary monomer of the multimeric peptide

<400> SEQUENCE: 41

Arg Lys Arg Pro His Ser Ile
1               5

<210> SEQ ID NO 42
<211> LENGTH: 7
<212> TYPE: PRT
<213> ORGANISM: Artificial sequence
<220> FEATURE:
<223> OTHER INFORMATION: Exemplary monomer of the multimeric peptide

<400> SEQUENCE: 42

Lys Arg Pro His Ser Ile Pro
1               5

<210> SEQ ID NO 43
<211> LENGTH: 7
<212> TYPE: PRT
<213> ORGANISM: Artificial sequence
<220> FEATURE:
<223> OTHER INFORMATION: Exemplary monomer of the multimeric peptide

<400> SEQUENCE: 43

Arg Pro His Ser Ile Pro Thr
1               5

<210> SEQ ID NO 44
<211> LENGTH: 7
<212> TYPE: PRT
<213> ORGANISM: Artificial sequence
<220> FEATURE:
<223> OTHER INFORMATION: Exemplary monomer of the multimeric peptide

<400> SEQUENCE: 44

Pro His Ser Ile Pro Thr Pro
1               5

<210> SEQ ID NO 45
<211> LENGTH: 7
<212> TYPE: PRT
<213> ORGANISM: Artificial sequence
<220> FEATURE:
<223> OTHER INFORMATION: Exemplary monomer of the multimeric peptide

<400> SEQUENCE: 45

His Ser Ile Pro Thr Pro Ile
1               5

<210> SEQ ID NO 46
<211> LENGTH: 7
<212> TYPE: PRT
<213> ORGANISM: Artificial sequence
<220> FEATURE:
<223> OTHER INFORMATION: Exemplary monomer of the multimeric peptide

<400> SEQUENCE: 46

Ser Ile Pro Thr Pro Ile Leu
1               5

<210> SEQ ID NO 47
<211> LENGTH: 7
<212> TYPE: PRT
<213> ORGANISM: Artificial sequence
<220> FEATURE:
<223> OTHER INFORMATION: Exemplary monomer of the multimeric peptide

<400> SEQUENCE: 47

Ile Pro Thr Pro Ile Leu Ile
1               5

<210> SEQ ID NO 48
<211> LENGTH: 7
<212> TYPE: PRT
<213> ORGANISM: Artificial sequence
<220> FEATURE:
<223> OTHER INFORMATION: Exemplary monomer of the multimeric peptide

<400> SEQUENCE: 48

Pro Thr Pro Ile Leu Ile Phe
1               5

<210> SEQ ID NO 49
<211> LENGTH: 7
<212> TYPE: PRT
<213> ORGANISM: Artificial sequence
<220> FEATURE:
<223> OTHER INFORMATION: Exemplary monomer of the multimeric peptide

<400> SEQUENCE: 49

Thr Pro Ile Leu Ile Phe Arg
1               5

<210> SEQ ID NO 50
<211> LENGTH: 7
<212> TYPE: PRT
<213> ORGANISM: Artificial sequence
<220> FEATURE:
<223> OTHER INFORMATION: Exemplary monomer of the multimeric peptide

<400> SEQUENCE: 50

Pro Ile Leu Ile Phe Arg Ser
1               5

<210> SEQ ID NO 51
<211> LENGTH: 7
<212> TYPE: PRT
<213> ORGANISM: Artificial sequence
<220> FEATURE:
<223> OTHER INFORMATION: Exemplary monomer of the multimeric peptide

<400> SEQUENCE: 51

Ile Leu Ile Phe Arg Ser Pro
1               5

```
<210> SEQ ID NO 52
<211> LENGTH: 8
<212> TYPE: PRT
<213> ORGANISM: Artificial sequence
<220> FEATURE:
<223> OTHER INFORMATION: Exemplary monomer of the multimeric peptide

<400> SEQUENCE: 52

His His Leu Leu Arg Pro Arg Arg
1               5

<210> SEQ ID NO 53
<211> LENGTH: 8
<212> TYPE: PRT
<213> ORGANISM: Artificial sequence
<220> FEATURE:
<223> OTHER INFORMATION: Exemplary monomer of the multimeric peptide

<400> SEQUENCE: 53

His Leu Leu Arg Pro Arg Arg Lys
1               5

<210> SEQ ID NO 54
<211> LENGTH: 8
<212> TYPE: PRT
<213> ORGANISM: Artificial sequence
<220> FEATURE:
<223> OTHER INFORMATION: Exemplary monomer of the multimeric peptide

<400> SEQUENCE: 54

Leu Leu Arg Pro Arg Arg Lys Arg
1               5

<210> SEQ ID NO 55
<211> LENGTH: 8
<212> TYPE: PRT
<213> ORGANISM: Artificial sequence
<220> FEATURE:
<223> OTHER INFORMATION: Exemplary monomer of the multimeric peptide

<400> SEQUENCE: 55

Leu Arg Pro Arg Arg Lys Arg Pro
1               5

<210> SEQ ID NO 56
<211> LENGTH: 8
<212> TYPE: PRT
<213> ORGANISM: Artificial sequence
<220> FEATURE:
<223> OTHER INFORMATION: Exemplary monomer of the multimeric peptide

<400> SEQUENCE: 56

Arg Pro Arg Arg Lys Arg Pro His
1               5

<210> SEQ ID NO 57
<211> LENGTH: 8
<212> TYPE: PRT
<213> ORGANISM: Artificial sequence
<220> FEATURE:
<223> OTHER INFORMATION: Exemplary monomer of the multimeric peptide

<400> SEQUENCE: 57

Pro Arg Arg Lys Arg Pro His Ser
1               5

<210> SEQ ID NO 58
```

```
<211> LENGTH: 8
<212> TYPE: PRT
<213> ORGANISM: Artificial sequence
<220> FEATURE:
<223> OTHER INFORMATION: Exemplary monomer of the multimeric peptide

<400> SEQUENCE: 58

Arg Arg Lys Arg Pro His Ser Ile
1               5

<210> SEQ ID NO 59
<211> LENGTH: 8
<212> TYPE: PRT
<213> ORGANISM: Artificial sequence
<220> FEATURE:
<223> OTHER INFORMATION: Exemplary monomer of the multimeric peptide

<400> SEQUENCE: 59

Arg Lys Arg Pro His Ser Ile Pro
1               5

<210> SEQ ID NO 60
<211> LENGTH: 8
<212> TYPE: PRT
<213> ORGANISM: Artificial sequence
<220> FEATURE:
<223> OTHER INFORMATION: Exemplary monomer of the multimeric peptide

<400> SEQUENCE: 60

Lys Arg Pro His Ser Ile Pro Thr
1               5

<210> SEQ ID NO 61
<211> LENGTH: 8
<212> TYPE: PRT
<213> ORGANISM: Artificial sequence
<220> FEATURE:
<223> OTHER INFORMATION: Exemplary monomer of the multimeric peptide

<400> SEQUENCE: 61

Arg Pro His Ser Ile Pro Thr Pro
1               5

<210> SEQ ID NO 62
<211> LENGTH: 8
<212> TYPE: PRT
<213> ORGANISM: Artificial sequence
<220> FEATURE:
<223> OTHER INFORMATION: Exemplary monomer of the multimeric peptide

<400> SEQUENCE: 62

Pro His Ser Ile Pro Thr Pro Ile
1               5

<210> SEQ ID NO 63
<211> LENGTH: 8
<212> TYPE: PRT
<213> ORGANISM: Artificial sequence
<220> FEATURE:
<223> OTHER INFORMATION: Exemplary monomer of the multimeric peptide

<400> SEQUENCE: 63

His Ser Ile Pro Thr Pro Ile Leu
1               5

<210> SEQ ID NO 64
<211> LENGTH: 8
```

```
<212> TYPE: PRT
<213> ORGANISM: Artificial sequence
<220> FEATURE:
<223> OTHER INFORMATION: Exemplary monomer of the multimeric peptide

<400> SEQUENCE: 64

Ser Ile Pro Thr Pro Ile Leu Ile
1               5

<210> SEQ ID NO 65
<211> LENGTH: 8
<212> TYPE: PRT
<213> ORGANISM: Artificial sequence
<220> FEATURE:
<223> OTHER INFORMATION: Exemplary monomer of the multimeric peptide

<400> SEQUENCE: 65

Ile Pro Thr Pro Ile Leu Ile Phe
1               5

<210> SEQ ID NO 66
<211> LENGTH: 8
<212> TYPE: PRT
<213> ORGANISM: Artificial sequence
<220> FEATURE:
<223> OTHER INFORMATION: Exemplary monomer of the multimeric peptide

<400> SEQUENCE: 66

Pro Thr Pro Ile Leu Ile Phe Arg
1               5

<210> SEQ ID NO 67
<211> LENGTH: 8
<212> TYPE: PRT
<213> ORGANISM: Artificial sequence
<220> FEATURE:
<223> OTHER INFORMATION: Exemplary monomer of the multimeric peptide

<400> SEQUENCE: 67

Thr Pro Ile Leu Ile Phe Arg Ser
1               5

<210> SEQ ID NO 68
<211> LENGTH: 8
<212> TYPE: PRT
<213> ORGANISM: Artificial sequence
<220> FEATURE:
<223> OTHER INFORMATION: Exemplary monomer of the multimeric peptide

<400> SEQUENCE: 68

Pro Ile Leu Ile Phe Arg Ser Pro
1               5

<210> SEQ ID NO 69
<211> LENGTH: 9
<212> TYPE: PRT
<213> ORGANISM: Artificial sequence
<220> FEATURE:
<223> OTHER INFORMATION: Exemplary monomer of the multimeric peptide

<400> SEQUENCE: 69

His His Leu Leu Arg Pro Arg Arg Lys
1               5

<210> SEQ ID NO 70
<211> LENGTH: 9
<212> TYPE: PRT
```

<213> ORGANISM: Artificial sequence
<220> FEATURE:
<223> OTHER INFORMATION: Exemplary monomer of the multimeric peptide

<400> SEQUENCE: 70

His Leu Leu Arg Pro Arg Arg Lys Arg
1               5

<210> SEQ ID NO 71
<211> LENGTH: 9
<212> TYPE: PRT
<213> ORGANISM: Artificial sequence
<220> FEATURE:
<223> OTHER INFORMATION: Exemplary monomer of the multimeric peptide

<400> SEQUENCE: 71

Leu Leu Arg Pro Arg Arg Lys Arg Pro
1               5

<210> SEQ ID NO 72
<211> LENGTH: 9
<212> TYPE: PRT
<213> ORGANISM: Artificial sequence
<220> FEATURE:
<223> OTHER INFORMATION: Exemplary monomer of the multimeric peptide

<400> SEQUENCE: 72

Leu Arg Pro Arg Arg Lys Arg Pro His
1               5

<210> SEQ ID NO 73
<211> LENGTH: 9
<212> TYPE: PRT
<213> ORGANISM: Artificial sequence
<220> FEATURE:
<223> OTHER INFORMATION: Exemplary monomer of the multimeric peptide

<400> SEQUENCE: 73

Arg Pro Arg Arg Lys Arg Pro His Ser
1               5

<210> SEQ ID NO 74
<211> LENGTH: 9
<212> TYPE: PRT
<213> ORGANISM: Artificial sequence
<220> FEATURE:
<223> OTHER INFORMATION: Exemplary monomer of the multimeric peptide

<400> SEQUENCE: 74

Pro Arg Arg Lys Arg Pro His Ser Ile
1               5

<210> SEQ ID NO 75
<211> LENGTH: 9
<212> TYPE: PRT
<213> ORGANISM: Artificial sequence
<220> FEATURE:
<223> OTHER INFORMATION: Exemplary monomer of the multimeric peptide

<400> SEQUENCE: 75

Arg Arg Lys Arg Pro His Ser Ile Pro
1               5

<210> SEQ ID NO 76
<211> LENGTH: 9
<212> TYPE: PRT
<213> ORGANISM: Artificial sequence

```
<220> FEATURE:
<223> OTHER INFORMATION: Exemplary monomer of the multimeric peptide

<400> SEQUENCE: 76

Arg Lys Arg Pro His Ser Ile Pro Thr
1               5

<210> SEQ ID NO 77
<211> LENGTH: 9
<212> TYPE: PRT
<213> ORGANISM: Artificial sequence
<220> FEATURE:
<223> OTHER INFORMATION: Exemplary monomer of the multimeric peptide

<400> SEQUENCE: 77

Lys Arg Pro His Ser Ile Pro Thr Pro
1               5

<210> SEQ ID NO 78
<211> LENGTH: 9
<212> TYPE: PRT
<213> ORGANISM: Artificial sequence
<220> FEATURE:
<223> OTHER INFORMATION: Exemplary monomer of the multimeric peptide

<400> SEQUENCE: 78

Arg Pro His Ser Ile Pro Thr Pro Ile
1               5

<210> SEQ ID NO 79
<211> LENGTH: 9
<212> TYPE: PRT
<213> ORGANISM: Artificial sequence
<220> FEATURE:
<223> OTHER INFORMATION: Exemplary monomer of the multimeric peptide

<400> SEQUENCE: 79

Pro His Ser Ile Pro Thr Pro Ile Leu
1               5

<210> SEQ ID NO 80
<211> LENGTH: 9
<212> TYPE: PRT
<213> ORGANISM: Artificial sequence
<220> FEATURE:
<223> OTHER INFORMATION: Exemplary monomer of the multimeric peptide

<400> SEQUENCE: 80

His Ser Ile Pro Thr Pro Ile Leu Ile
1               5

<210> SEQ ID NO 81
<211> LENGTH: 9
<212> TYPE: PRT
<213> ORGANISM: Artificial sequence
<220> FEATURE:
<223> OTHER INFORMATION: Exemplary monomer of the multimeric peptide

<400> SEQUENCE: 81

Ser Ile Pro Thr Pro Ile Leu Ile Phe
1               5

<210> SEQ ID NO 82
<211> LENGTH: 9
<212> TYPE: PRT
<213> ORGANISM: Artificial sequence
<220> FEATURE:
```

```
<223> OTHER INFORMATION: Exemplary monomer of the multimeric peptide

<400> SEQUENCE: 82

Ile Pro Thr Pro Ile Leu Ile Phe Arg
1               5

<210> SEQ ID NO 83
<211> LENGTH: 9
<212> TYPE: PRT
<213> ORGANISM: Artificial sequence
<220> FEATURE:
<223> OTHER INFORMATION: Exemplary monomer of the multimeric peptide

<400> SEQUENCE: 83

Pro Thr Pro Ile Leu Ile Phe Arg Ser
1               5

<210> SEQ ID NO 84
<211> LENGTH: 9
<212> TYPE: PRT
<213> ORGANISM: Artificial sequence
<220> FEATURE:
<223> OTHER INFORMATION: Exemplary monomer of the multimeric peptide

<400> SEQUENCE: 84

Thr Pro Ile Leu Ile Phe Arg Ser Pro
1               5

<210> SEQ ID NO 85
<211> LENGTH: 10
<212> TYPE: PRT
<213> ORGANISM: Artificial sequence
<220> FEATURE:
<223> OTHER INFORMATION: Exemplary monomer of the multimeric peptide

<400> SEQUENCE: 85

His His Leu Leu Arg Pro Arg Arg Lys Arg
1               5                   10

<210> SEQ ID NO 86
<211> LENGTH: 10
<212> TYPE: PRT
<213> ORGANISM: Artificial sequence
<220> FEATURE:
<223> OTHER INFORMATION: Exemplary monomer of the multimeric peptide

<400> SEQUENCE: 86

His Leu Leu Arg Pro Arg Arg Lys Arg Pro
1               5                   10

<210> SEQ ID NO 87
<211> LENGTH: 10
<212> TYPE: PRT
<213> ORGANISM: Artificial sequence
<220> FEATURE:
<223> OTHER INFORMATION: Exemplary monomer of the multimeric peptide

<400> SEQUENCE: 87

Leu Leu Arg Pro Arg Arg Lys Arg Pro His
1               5                   10

<210> SEQ ID NO 88
<211> LENGTH: 10
<212> TYPE: PRT
<213> ORGANISM: Artificial sequence
<220> FEATURE:
<223> OTHER INFORMATION: Exemplary monomer of the multimeric peptide
```

<400> SEQUENCE: 88

Leu Arg Pro Arg Arg Lys Arg Pro His Ser
1               5                   10

<210> SEQ ID NO 89
<211> LENGTH: 10
<212> TYPE: PRT
<213> ORGANISM: Artificial sequence
<220> FEATURE:
<223> OTHER INFORMATION: Exemplary monomer of the multimeric peptide

<400> SEQUENCE: 89

Arg Pro Arg Arg Lys Arg Pro His Ser Ile
1               5                   10

<210> SEQ ID NO 90
<211> LENGTH: 10
<212> TYPE: PRT
<213> ORGANISM: Artificial sequence
<220> FEATURE:
<223> OTHER INFORMATION: Exemplary monomer of the multimeric peptide

<400> SEQUENCE: 90

Pro Arg Arg Lys Arg Pro His Ser Ile Pro
1               5                   10

<210> SEQ ID NO 91
<211> LENGTH: 10
<212> TYPE: PRT
<213> ORGANISM: Artificial sequence
<220> FEATURE:
<223> OTHER INFORMATION: Exemplary monomer of the multimeric peptide

<400> SEQUENCE: 91

Arg Arg Lys Arg Pro His Ser Ile Pro Thr
1               5                   10

<210> SEQ ID NO 92
<211> LENGTH: 10
<212> TYPE: PRT
<213> ORGANISM: Artificial sequence
<220> FEATURE:
<223> OTHER INFORMATION: Exemplary monomer of the multimeric peptide

<400> SEQUENCE: 92

Arg Lys Arg Pro His Ser Ile Pro Thr Pro
1               5                   10

<210> SEQ ID NO 93
<211> LENGTH: 10
<212> TYPE: PRT
<213> ORGANISM: Artificial sequence
<220> FEATURE:
<223> OTHER INFORMATION: Exemplary monomer of the multimeric peptide

<400> SEQUENCE: 93

Lys Arg Pro His Ser Ile Pro Thr Pro Ile
1               5                   10

<210> SEQ ID NO 94
<211> LENGTH: 10
<212> TYPE: PRT
<213> ORGANISM: Artificial sequence
<220> FEATURE:
<223> OTHER INFORMATION: Exemplary monomer of the multimeric peptide

```
<400> SEQUENCE: 94

Arg Pro His Ser Ile Pro Thr Pro Ile Leu
 1               5                  10

<210> SEQ ID NO 95
<211> LENGTH: 10
<212> TYPE: PRT
<213> ORGANISM: Artificial sequence
<220> FEATURE:
<223> OTHER INFORMATION: Exemplary monomer of the multimeric peptide

<400> SEQUENCE: 95

Pro His Ser Ile Pro Thr Pro Ile Leu Ile
 1               5                  10

<210> SEQ ID NO 96
<211> LENGTH: 10
<212> TYPE: PRT
<213> ORGANISM: Artificial sequence
<220> FEATURE:
<223> OTHER INFORMATION: Exemplary monomer of the multimeric peptide

<400> SEQUENCE: 96

His Ser Ile Pro Thr Pro Ile Leu Ile Phe
 1               5                  10

<210> SEQ ID NO 97
<211> LENGTH: 10
<212> TYPE: PRT
<213> ORGANISM: Artificial sequence
<220> FEATURE:
<223> OTHER INFORMATION: Exemplary monomer of the multimeric peptide

<400> SEQUENCE: 97

Ser Ile Pro Thr Pro Ile Leu Ile Phe Arg
 1               5                  10

<210> SEQ ID NO 98
<211> LENGTH: 10
<212> TYPE: PRT
<213> ORGANISM: Artificial sequence
<220> FEATURE:
<223> OTHER INFORMATION: Exemplary monomer of the multimeric peptide

<400> SEQUENCE: 98

Ile Pro Thr Pro Ile Leu Ile Phe Arg Ser
 1               5                  10

<210> SEQ ID NO 99
<211> LENGTH: 10
<212> TYPE: PRT
<213> ORGANISM: Artificial sequence
<220> FEATURE:
<223> OTHER INFORMATION: Exemplary monomer of the multimeric peptide

<400> SEQUENCE: 99

Pro Thr Pro Ile Leu Ile Phe Arg Ser Pro
 1               5                  10

<210> SEQ ID NO 100
<211> LENGTH: 48
<212> TYPE: PRT
<213> ORGANISM: Artificial sequence
<220> FEATURE:
<223> OTHER INFORMATION: Placental Immunoregulatory Ferritin (PLIF), C',
      derived peptide C48
```

```
<400> SEQUENCE: 100

Phe Pro Ser Pro Ile Ser Pro Ser Pro Ser Cys Trp His His Tyr Thr
1               5                   10                  15

Thr Asn Arg Pro Gln Pro Gln His His Leu Leu Arg Pro Arg Arg Arg
            20              25                  30

Lys Arg Pro His Ser Ile Pro Thr Pro Ile Leu Ile Phe Arg Ser Pro
        35              40                  45
```